(12) United States Patent
 Ariyama et al.

(10) Patent No.: US 11,986,334 B2
(45) Date of Patent: May 21, 2024

(54) MEDICAL APPARATUS AND PROGRAM

(71) Applicant: GE Precision Healthcare LLC, Wauwatosa, WI (US)

(72) Inventors: Naoki Ariyama, Tokyo (JP); Yoshio Takaichi, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 188 days.

(21) Appl. No.: 17/485,009

(22) Filed: Sep. 24, 2021

(65) Prior Publication Data
US 2022/0096029 A1    Mar. 31, 2022

(30) Foreign Application Priority Data
Sep. 25, 2020 (JP) .................................. 2020-161496

(51) Int. Cl.
*A61B 6/00* (2006.01)
*A61B 6/03* (2006.01)
*A61B 6/46* (2024.01)

(52) U.S. Cl.
CPC .............. *A61B 6/468* (2013.01); *A61B 6/032* (2013.01); *A61B 6/461* (2013.01); *A61B 6/5205* (2013.01); *A61B 6/54* (2013.01)

(58) Field of Classification Search
CPC ....... A61B 6/542; A61B 6/566; A61B 5/7405; A61B 5/7475; A61B 5/7465; A61B 8/565; A61B 5/002; A61B 5/113; A61B 2090/371; A61B 2017/00203; A61B 34/25; A61B 6/54; A61B 2560/0271; G16H 80/00; G16H 40/67; G16H 10/60; G16H 20/40; G16H 50/20; H04Q 5/24
See application file for complete search history.

(56) References Cited

U.S. PATENT DOCUMENTS 5,384,537 A      1/1995  Ito
2014/0372136 A1  12/2014 Lee

FOREIGN PATENT DOCUMENTS

CN      201274518 Y  *  7/2009
JP       05305067 A      11/1993
(Continued)

OTHER PUBLICATIONS

JP application 2020-161496 filed Sep. 25, 2020—Office Action dated Nov. 16, 2021, Machine Translation; 3 pages.
(Continued)

*Primary Examiner* — Don K Wong

(57) ABSTRACT

To provide a technique with which an operator, when talking into a microphone, can recognize whether or not his/her voice is being output from a speaker in a scan room, a CT apparatus 1 has: an operator microphone 41 installed in an operation room R2 for receiving a voice of an operator 81; a patient microphone 2 installed in a scan room R1 for receiving a voice of a patient 80; a speaker 50 installed in the operation room R2 for outputting the voice of the patient 80 received by the patient microphone 2; a speaker 5 installed in the scan room R1 for outputting the voice of the operator 81 received by the operator microphone 41; and a light-emitting section 31 for informing, in the case that the patient microphone 2 has received the voice of the operator 81 output from the speaker 5, the operator 81 that his/her voice is being output from the speaker 5.

18 Claims, 22 Drawing Sheets

(56) References Cited

FOREIGN PATENT DOCUMENTS

| | | | |
|---|---|---|---|
| JP | 0657318 B2 | 8/1994 | |
| JP | 2003265454 A | 9/2003 | |
| JP | 2004041489 A * | 2/2004 | |
| WO | WO-2022050459 A1 * | 3/2022 | ........... G06T 1/0021 |

OTHER PUBLICATIONS

EP application 21196435.8 filed Sep. 13, 2021—Search Report dated Feb. 9, 2022; 8 pages.
JP-H0657318—English; TXPMTJEU; 4 pages.

* cited by examiner

MEDICAL APPARATUS AND PROGRAM

CROSS-REFERENCE TO RELATED APPLICATIONS

This application claims priority to Japanese Patent Application No. 2020-161496, filed on Sep. 25, 2020, the disclosure of which is incorporated herein by reference in its entirety.

BACKGROUND

The present invention relates to a medical apparatus having a communication device for allowing communication between a patient and an operator, and a program stored in the medical apparatus.

An X-ray CT apparatus is known as a medical apparatus for non-invasively imaging the inside of a patient. Because of its ability to image a body part to be imaged in a short time, the X-ray CT apparatus is widely used in medical institutions, such as hospitals.

A CT apparatus has a gantry and a table as its main components. The gantry and table are disposed in a scan room. The gantry is provided with a rotating section on which an X-ray tube and a detector are mounted. In imaging a patient, a scan is performed while rotating the rotating section. The CT apparatus also has an operator console for operating the gantry and table, the operator console being disposed in an operation room provided separately from the scan room. The operator can control the gantry and table by operating the operator console disposed in the operation room.

The CT apparatus moreover has a communication device allowing the operator in the operation room to communicate with the patient in the scan room. The communication device has a microphone for receiving an operator's voice, and a speaker for transmitting the voice received by the microphone to the patient in the scan room.

When the operator utters a voice, the microphone receives the operator's voice, causing the operator's voice to be generated from the speaker. Accordingly, the patient can hear the operator's voice while in the scan room.

However, in the case that the communication device is set to an "OFF" mode in which no communication is made, or some failure occurs in the communication device, for example, when the operator in the operation room talks into the microphone about requirements for an examination, the operator's voice is not output from the speaker in the scan room. Accordingly, when talking into the microphone and receiving no response from the patient, the operator may sometimes be worried that the voice of his/her own is not output from the speaker in the scan room. At other times, the operator may not be aware that the voice of his/her own is not output from the speaker in the scan room.

Accordingly, it is desirable to enable the operator to, when talking into a microphone, recognize whether or not the voice of his/her own is being output from the speaker in the scan room.

SUMMARY

In a first aspect, a medical apparatus comprises a first microphone installed in a first room for receiving a voice of an operator; a second microphone installed in a second room for receiving a voice of a patient; a first speaker installed in the first room for outputting the voice of the patient received by the second microphone; a second speaker installed in the second room for outputting the voice of the operator received by the first microphone; and when the second microphone has received the voice of the operator output from the second speaker, informing the operator that the voice of the operator is being output from the second speaker.

In a second aspect, a program stored in a medical apparatus, the apparatus comprising a first microphone installed in a first room for receiving a voice of an operator; a second microphone installed in a second room for receiving a voice of a patient; a first speaker installed in the first room for outputting the voice of the patient received by the second microphone; a second speaker installed in the second room for outputting the voice of the operator received by the first microphone; and when the second microphone has received the voice of the operator output from the second speaker, informing the operator that the voice of the operator is being output from the second speaker, the program being for causing one or more processors to execute processing of receiving a first digital signal containing sound data representing a sound that the first microphone has received, and a second digital signal containing sound data representing a sound that the second microphone has received, generating from the second digital signal a third digital signal representing signal components corresponding to noise, and generating a fourth digital signal containing sound data representing the voice of the operator by subtracting the third digital signal from the second digital signal; and control processing of controlling the informing of the operator based on the fourth digital signal.

In a third aspect, is a non-transitory, computer-readable recording medium provided in a medical apparatus, the apparatus comprising a first microphone installed in a first room for receiving a voice of an operator; a second microphone installed in a second room for receiving a voice of a patient; a first speaker installed in the first room for outputting the voice of the patient received by the second microphone; a second speaker installed in the second room for outputting the voice of the operator received by the first microphone; and when the second microphone has received the voice of the operator output from the second speaker, informing the operator that the voice of the operator is being output from the second speaker, in the recording medium are stored one or more instructions executable by one or more processors, the one or more instructions, when executed by the one or more processors, causing the one or more processors to execute an operation comprising the acts of receiving a first digital signal containing sound data representing a sound that the first microphone has received; receiving a second digital signal containing sound data representing a sound that the second microphone has received; generating from the second digital signal a third digital signal representing signal components corresponding to noise; generating a fourth digital signal containing sound data representing the voice of the operator by subtracting the third digital signal from the second digital signal; and controlling the informing of the operator based on the fourth digital signal.

The second speaker outputs a voice of the operator in the first room. When the operator's voice is output from the second speaker, the second microphone receives the voice output from the second speaker. The medical apparatus includes, when the second microphone has received the voice of the operator output from the second speaker, informing the operator that the voice of the operator is being output from the second speaker. Accordingly, when the operator's voice is output from the second speaker, the operator can recognize while in the first room that the voice is being output from the second speaker. Thus, the operator is freed from worry that the voice of his/her own may not be heard by the patient, and therefore, the operator can concentrate on his/her work to smoothly achieve a scan on the patient.

DETAILED DESCRIPTION

Figure 1:
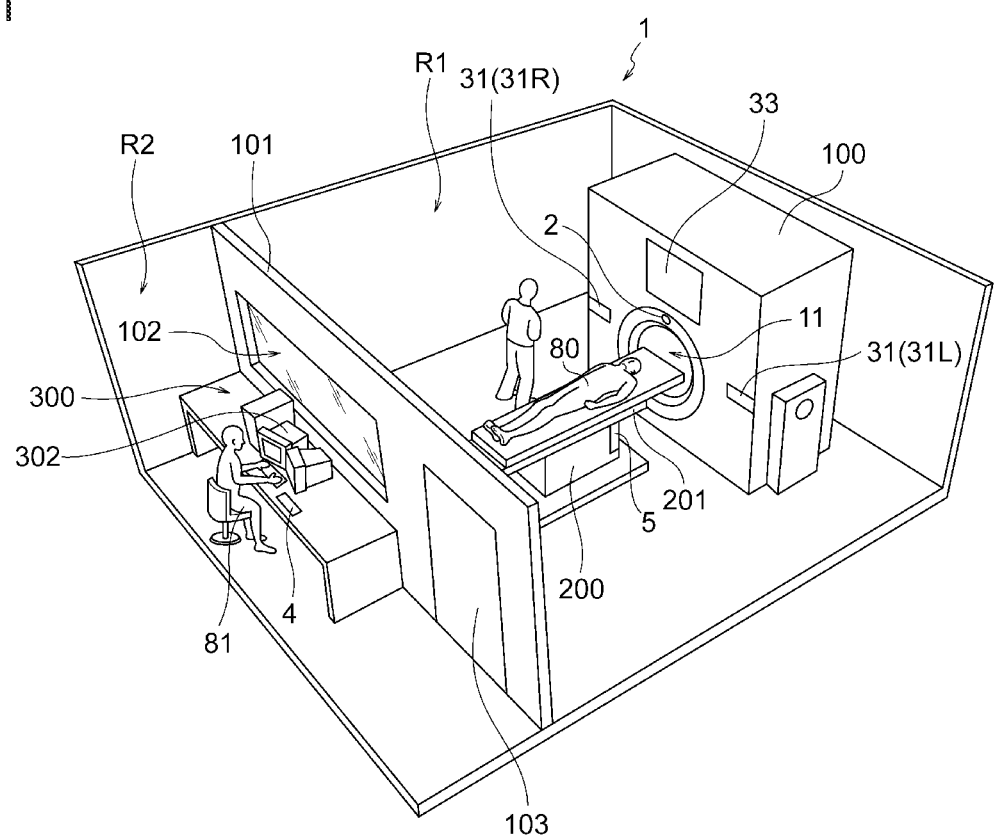
FIG. 1 is a perspective view of an exemplary embodiment of an X-ray CT apparatus.

FIG. 1 is a perspective view of an exemplary embodiment of an X-ray CT apparatus.

As shown in FIG. 1, an X-ray CT apparatus 1 comprises a gantry 100, a table 200, and an operator console 300.

The gantry 100 and table 200 are installed in a scan room R1. The operator console 300 is installed in an operation room R2 separate from the scan room R1. In FIG. 1, ceilings and some sidewalls of the scan room R1 and operation room R2 are omitted from the drawing for convenience of explanation.

The scan room R1 and operation room R2 are separated from each other by a wall 101. The wall 101 is provided with a window 102 allowing an operator 81 to view the scan room R1 from the operation room R2. The wall 101 is also provided with a door 103 for allowing the operator 81 to move between the scan room R1 and operation room R2.

The wall 101 and window 102 lying between the scan room R1 and operation room R2 can have any shape, and moreover, various materials may be used as a material(s) making up the wall and window, insofar as satisfactory safety of a human body can be ensured.

The gantry 100 is provided on its front surface with a display section 33. The display section 33 is capable of displaying patient information, information helpful for preparation for a scan, and/or the like. Accordingly, the operator can smoothly prepare for a scan on a patient 80 while checking over the display on the display section 33.

Figure 2:
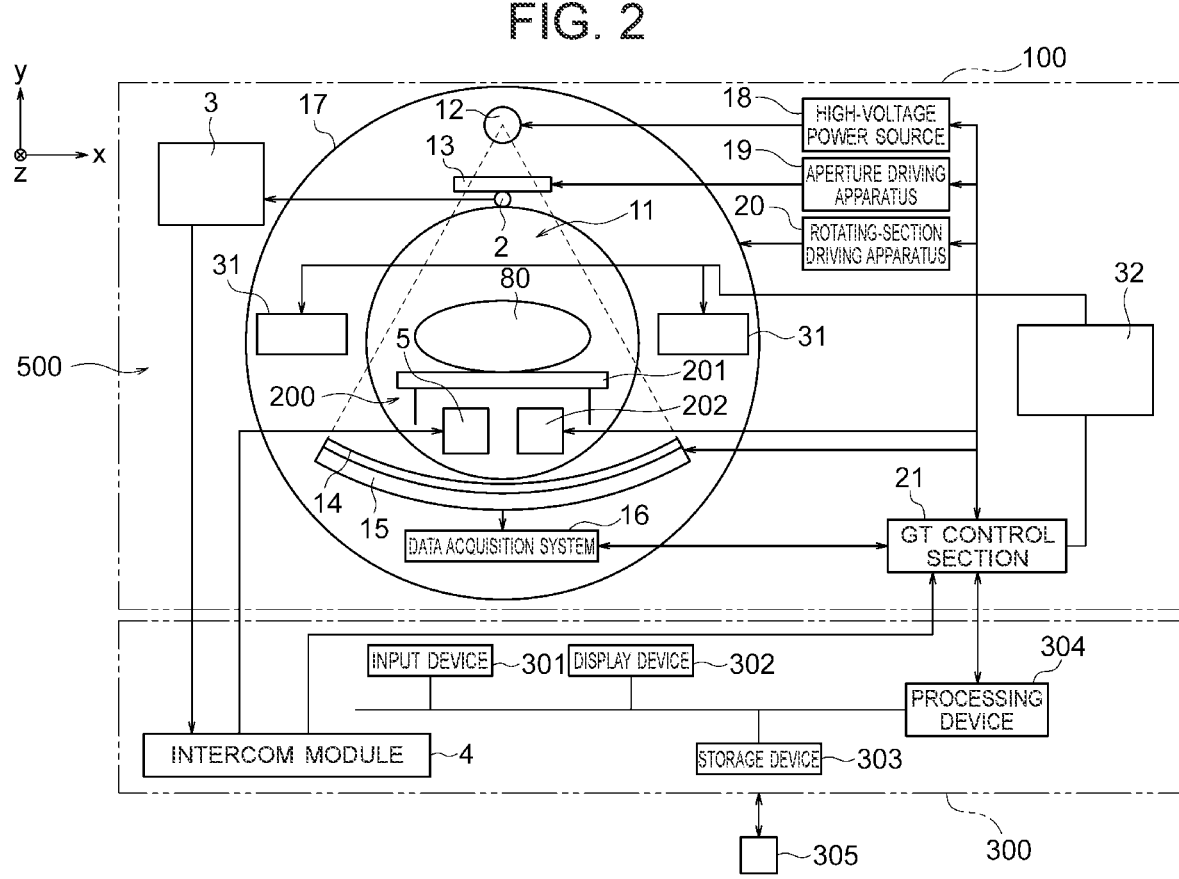
FIG. 2 is a diagram schematically showing a hardware configuration of an X-ray CT apparatus in accordance with an exemplary embodiment.

FIG. 2 is a diagram schematically showing a hardware configuration of an X-ray CT apparatus in accordance with an exemplary embodiment.

The gantry 100 has a bore 11 for forming space through which the patient 80 can be moved.

The gantry 100 also has an X-ray tube 12, an aperture 13, a collimator device 14, an X-ray detector 15, a data acquisition system 16, a rotating section 17, a high-voltage power source 18, an aperture driving apparatus 19, a rotation driving apparatus 20, a GT (Gantry Table) control section 21, etc.

The rotating section 17 is constructed to be rotatable around the bore 11.

The rotating section 17 has the X-ray tube 12, aperture 13, collimator device 14, X-ray detector 15, and data acquisition system 16 mounted thereon.

The X-ray tube 12 and X-ray detector 15 are disposed to face each other across the bore 11 of the gantry 100.

The aperture 13 is disposed between the X-ray tube 12 and bore 11. The aperture 13 shapes X-rays emitted from an X-ray focus of the X-ray tube 12 toward the X-ray detector 15 into a fan beam or a cone beam.

The collimator device 14 is disposed between the bore 11 and X-ray detector 15.

The collimator device 14 removes scatter rays entering the X-ray detector 15.

The X-ray detector 15 has a plurality of X-ray detector elements two-dimensionally arranged in directions of the extent and thickness of the fan-shaped X-ray beam emitted from the X-ray tube 12. Each X-ray detector element detects X-rays passing through the patient 80, and outputs an electrical signal depending upon the intensity thereof.

The data acquisition system 16 receives electrical signals output from the X-ray detector elements in the X-ray detector 15, and converts them into X-ray data for acquisition.

The table 200 has a cradle 201 and a driving apparatus 202. The patient 80 lies on the cradle 201. The driving apparatus 202 drives the table 200 and cradle 201 so that the cradle 201 can move in y- and z-directions.

The high-voltage power source 18 supplies high voltage and electric current to the X-ray tube 12.

The aperture driving apparatus 19 drives the aperture 13 to modify the shape of its opening.

The rotation driving apparatus 20 rotationally drives the rotating section 17.

The GT control section 21 executes processing for controlling several apparatuses/devices and several sections in the gantry 100, the driving apparatus 202 for the table 200, etc. The GT control section 21 also supplies to a light-emission control section 32 a signal carrying thereon information necessary for controlling a light-emitting section 31. The light-emission control section 32 and light-emitting section 31 will be discussed later.

The operator console 300 accepts several kinds of operations from the operator. The operator console 300 has an input device 301, a display device 302, a storage device 303, a processing device 304, and an intercom module 4.

The input device 301 may comprise buttons and a keyboard for accepting an input of a command and information from the operator, and a pointing device, such as a mouse. The display device 302 is an LCD (Liquid Crystal Display), an organic EL (Electro-Luminescence) display, or the like.

The storage device 303 may comprise a HDD (Hard Disk Drive), semiconductor memory such as RAM (Random Access Memory) and ROM (Read Only Memory), etc. The operator console 300 may have all of the HDD, RAM, and ROM as the storage device 303. The storage device 303 may also comprise a portable storage medium 305, such as a CD (Compact Disk) or a DVD (Digital Versatile Disk).

The processing device 304 comprises a processor for executing several kinds of processing.

The intercom module 4 is used when the operator 81 communicates with the patient 80. The intercom module 4 will be described in detail later.

The CT apparatus 1 moreover has a communication device 500 for allowing the operator 81 in the operation room R2 and the patient 80 in the scan room R1 to communicate with each other.

The communication device 500 has a patient microphone 2, an amplifier board 3, an intercom module 4, and a speaker 5. Now the communication device 500 will be described with reference to FIG. 3, as well as FIG. 2.

Figure 3:
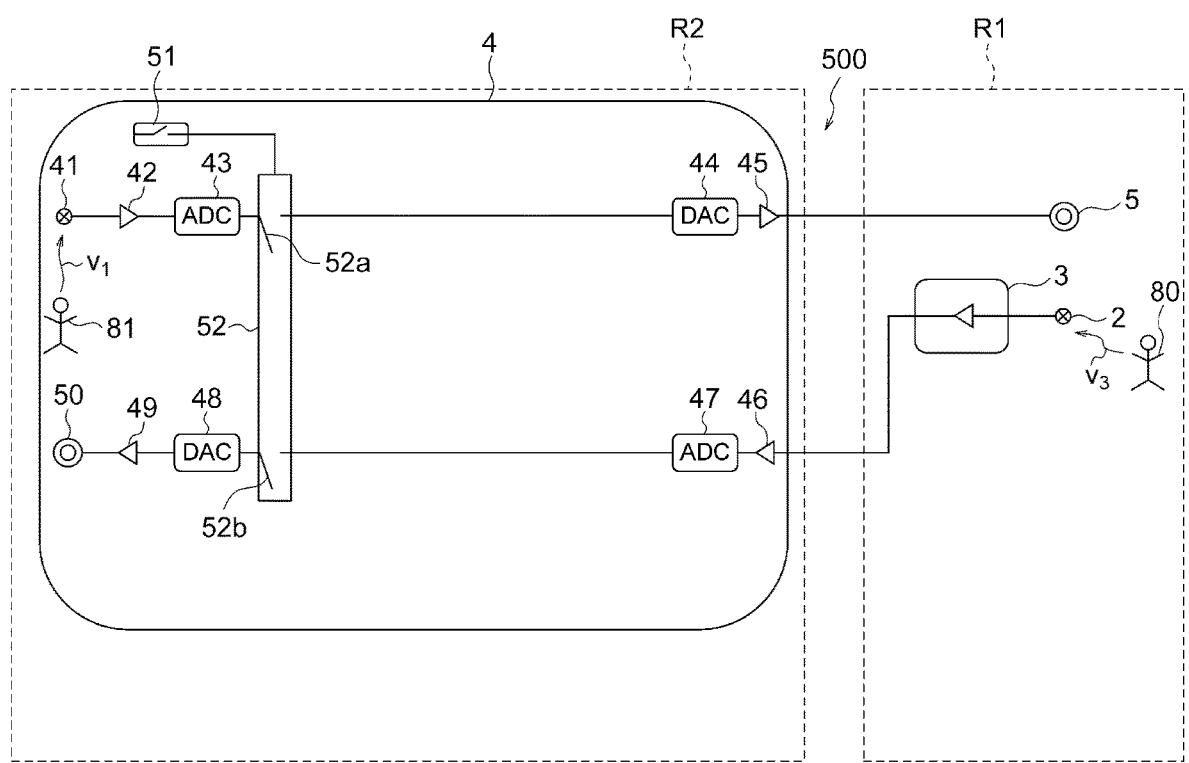
FIG. 3 is a circuit diagram of a communication device.

FIG. 3 is a circuit diagram of the communication device 500.

In FIG. 3, the scan room R1 and operation room R2 are each designated by dashed lines.

In the scan room R1 are disposed the patient microphone 2, speaker 5, and amplifier board 3 of the communication device 500.

The patient microphone 2 is for receiving a voice of the patient 80. The patient microphone 2 can be installed in the proximity of the bore 11 of the gantry 100, as shown in FIG. 1. The patient microphone 2 is, however, not necessarily installed in the gantry 100, and may be installed at a different place from the gantry 100 (e.g., in the table 200, or on the wall or ceiling of the scan room R1) insofar as it can receive the voice of the patient 80.

The speaker 5 is for outputting a voice of the operator 81 in the operation room R2. The speaker 5 may be installed under the cradle 201 of the table 200, as shown in FIG. 1. The speaker 5 is, however, not necessarily installed in the table 200, and may be installed at a different place from the table 200 (e.g., in the gantry 100, or on the wall or ceiling of the scan room R1) insofar as the patient 80 can hear the voice from the speaker 5.

Returning to FIG. 3, the description will be continued.

The amplifier board 3 amplifies a signal of a sound received by the patient microphone 2. The amplifier board 3 may be installed in the inside of the gantry 100.

On the other hand, in the operation room R2 is disposed the intercom module 4 of the communication device 500.

As shown in FIG. 3, the intercom module 4 has an operator microphone 41, a preamplifier 42, an ADC (Analog-to-Digital Converter) 43, a DAC (Digital-to-Analog Converter) 44, a power amplifier 45, a buffer amplifier 46, an ADC 47, a DAC 48, a power amplifier 49, a speaker 50, a microphone switch 51, and a switch section 52. While the intercom module 4 comprises circuit parts, several kinds of switches, and several kinds of buttons in addition to the components 41 to 52, they are omitted in the drawings because they are not needed for the description of the present invention.

The switch section 52 has two switching elements 52a and 52b.

The switching element 52a is provided between the ADC 43 and DAC 44. When the switching element 52a is set to "ON," the switching element 52a electrically connects the ADC 43 and the DAC 44 together, and when the switching element 52a is set to "OFF," the ADC 43 is electrically disconnected from the DAC 44.

On the other hand, the switching element 52b is provided between the ADC 47 and DAC 48. When the switching element 52b is set to "ON," the switching element 52b electrically connects the ADC 47 and the DAC 48 together, and when the switching element 52b is set to "OFF," the ADC 47 is electrically disconnected from the DAC 48.

Figure 4:
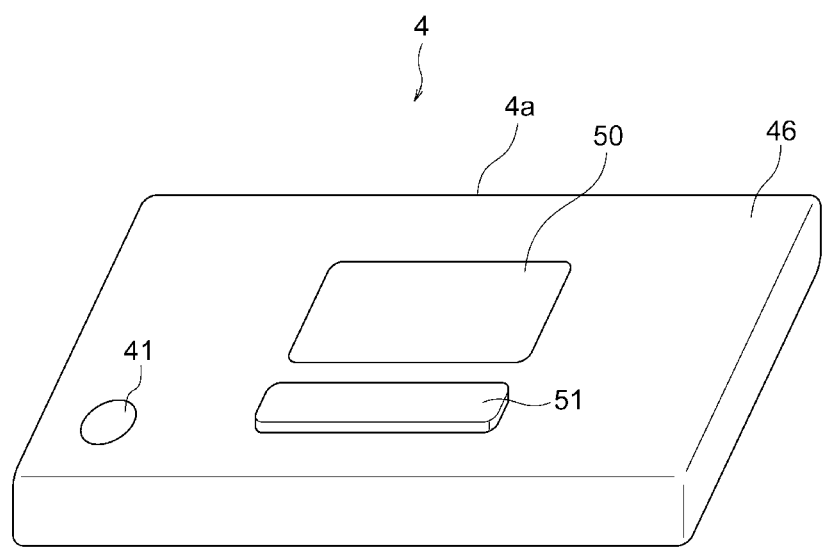
FIG. 4 is a perspective view of an appearance of an intercom module.

FIG. 4 is a perspective view of an appearance of the intercom module 4. The intercom module 4 has a generally rectangular parallelepiped-shaped housing 4a. The housing 4a has the components 41 to 51 (see FIG. 3) of the intercom module 4 incorporated therein. In FIG. 4, three of the components 41 to 51, i.e., the operator microphone 41, speaker 50, and microphone switch 51, are shown. The microphone switch 51 is provided on an upper surface 4b of the housing 4a. The microphone switch 51 is a switch for changing the communication mode of the intercom module 4. Here, the microphone switch 51 is constructed to allow the operator 81 to press it, and the communication mode of the intercom module 4 can be changed by the operator 81 pressing the microphone switch 51 as needed. Now the communication mode of the intercom module 4 will be described hereinbelow.

Figure 5:
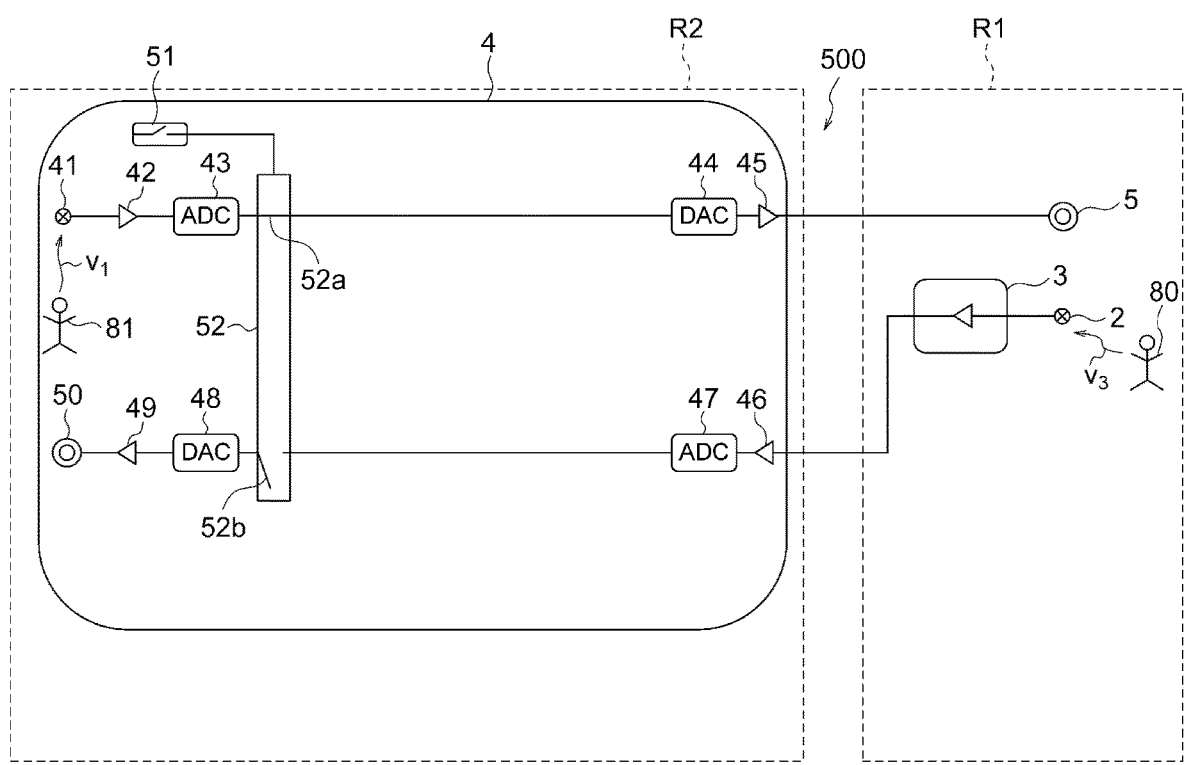
FIG. 5 is a diagram showing the intercom module set to a first communication mode.

When the operator 81 has pressed the microphone switch 51, the mode is set to a first communication mode in which the voice of the operator 81 can be transmitted to the patient 80. FIG. 5 is a diagram showing the intercom module 4 set to the first communication mode. When the microphone switch 51 is pressed, the switching element 52a in the switch section 52 is set to "ON," and thus, the operator microphone 41 and speaker 5 are electrically connected with each other. Accordingly, by continuously pressing the microphone switch 51, the operator 81 can transmit the voice of his/her own to the patient 80 while the microphone switch 51 is pressed.

While the microphone switch 51 is pressed, the switching element 52b is set to "OFF." Accordingly, the patient microphone 2 is electrically disconnected from the speaker 50, and thus, no sound is output from the speaker 50 in the first communication mode.

Figure 6:
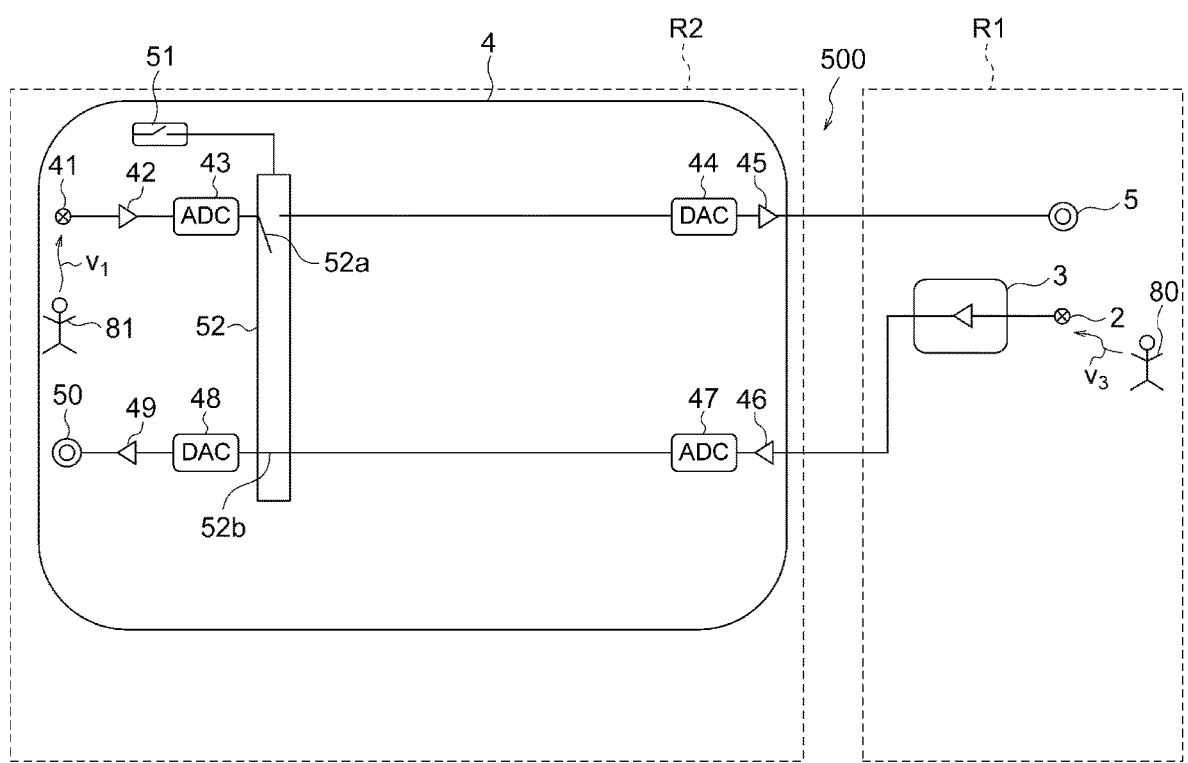
FIG. 6 is a diagram showing the intercom module set to a second communication mode.

On the other hand, when the operator 81 is not pressing the microphone switch 51, the mode is set to a second communication mode in which the voice of the patient 80 can be transmitted to the operator 81. FIG. 6 is a diagram showing the intercom module 4 set to the second communication mode. The switching element 52b is in "ON" when the operator 81 is not pressing the microphone switch 51 in the present embodiment. Accordingly, in the second communication mode, the patient microphone 2 and speaker 50 are in an electrically connected state. Thus, when the patient 80 utters a voice, the voice of the patient 80 is received by the patient microphone 2 and is output to the speaker 50, so that the operator 81 can hear the voice of the patient 80 while in the operation room R2.

The switching element 52a is in "OFF" when the operator 81 is not pressing the microphone switch 51. Accordingly, the operator microphone 41 is a state electrically disconnected from the speaker 5. Thus, in the second communication mode, no sound is output from the speaker 5.

As described above, the intercom module 4 has two communication modes, and the operator 81 can change the communication mode by the microphone switch 51 to thereby allow communication between the operator 81 and patient 80.

Now an operation of the communication device 500 in the first communication mode and that in the second communication mode will be described one by one hereinbelow.

Figure 7:
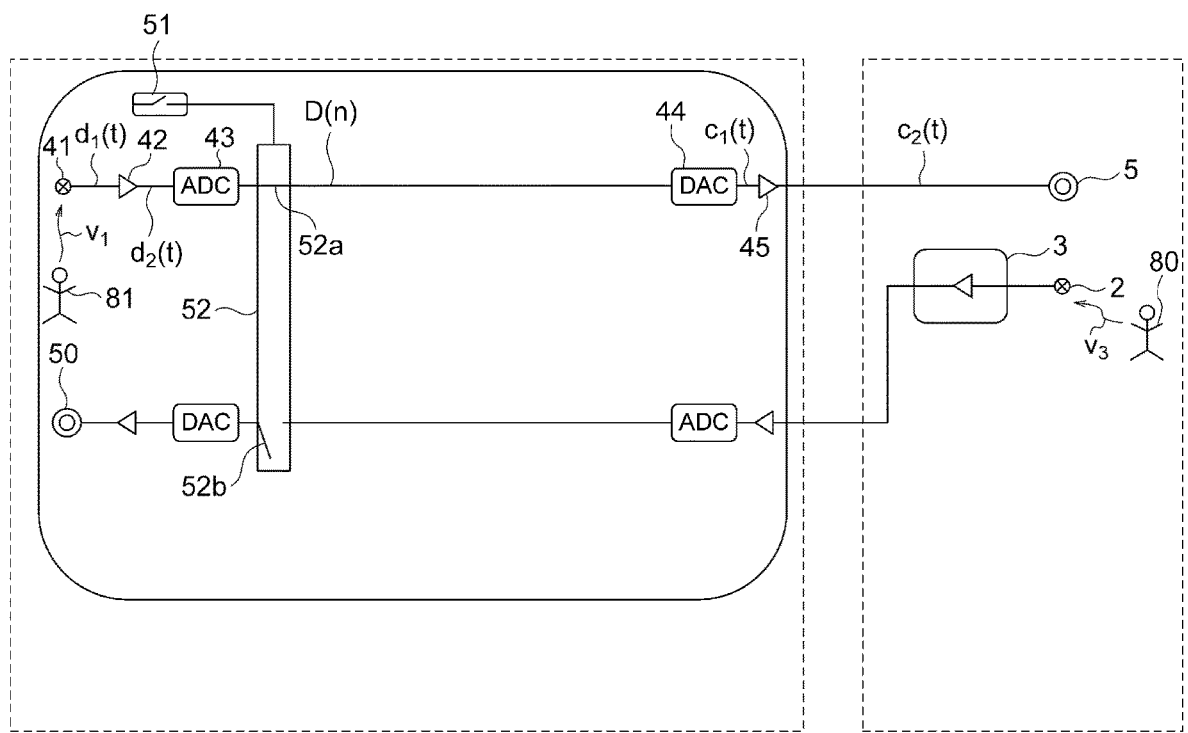
FIG. 7 is an explanatory diagram for the first communication mode.

FIG. 7 is an explanatory diagram for the first communication mode.

To set the intercom module 4 to the first communication mode, the operator 81 continuously presses the microphone switch 51. While the operator 81 is pressing the microphone switch 51, the switching element 52a is set to "ON" and the switching element 52b is set to "OFF," as shown in FIG. 7. Accordingly, in the first communication mode, the patient microphone 2 is set to a state electrically disconnected from the speaker 50 while the operator microphone 41 is set to a state electrically connected to the speaker 5. Thus, in the first communication mode, by the operator 81 talking into the operator microphone 41, the patient 80 can hear the voice of the patient 80 from the speaker 5. In the first communication mode, the intercom module 4 operates as follows.

When the operator 81 utters a voice v1, the operator microphone 41 receives the voice v1 of the operator 81. Upon receiving the voice v1, the operator microphone 41 outputs an analog signal d1($t$) representing the received voice v1.

The preamplifier 42 receives the analog signal d1($t$) output from the operator microphone 41, and amplifies the received analog signal d1($t$). The preamplifier 42 amplifies the analog signal d1($t$) from the operator microphone 41 up to an input voltage range for the ADC 43 at the following stage.

The ADC 43 converts an analog signal d2($t$) output from the preamplifier 42 into a digital signal D(n).

Accordingly, a circuitry part constituted by the preamplifier 42 and ADC 43 operates as a circuitry part that generates the digital signal D(n) based on the analog signal d1($t$).

The DAC 44 converts the digital signal D(n) from the ADC 43 into an analog signal c1($t$).

The power amplifier 45 receives the analog signal c1($t$) from the DAC 44, amplifies the received analog signal c1($t$), and outputs the resulting signal as an analog signal c2($t$). The analog signal c2($t$) is supplied to the speaker 5. Accordingly, a circuitry part constituted by the DAC 44 and power amplifier 45 operates as a circuitry part that generates the analog signal c2($t$) to be supplied to the speaker 5 based on the digital signal D(n).

The speaker 5 receives the analog signal c2($t$) output from the power amplifier 45, and outputs a sound corresponding to the received analog signal c2($t$).

Accordingly, the patient 80 can hear the voice of the operator 81.

Figure 8:
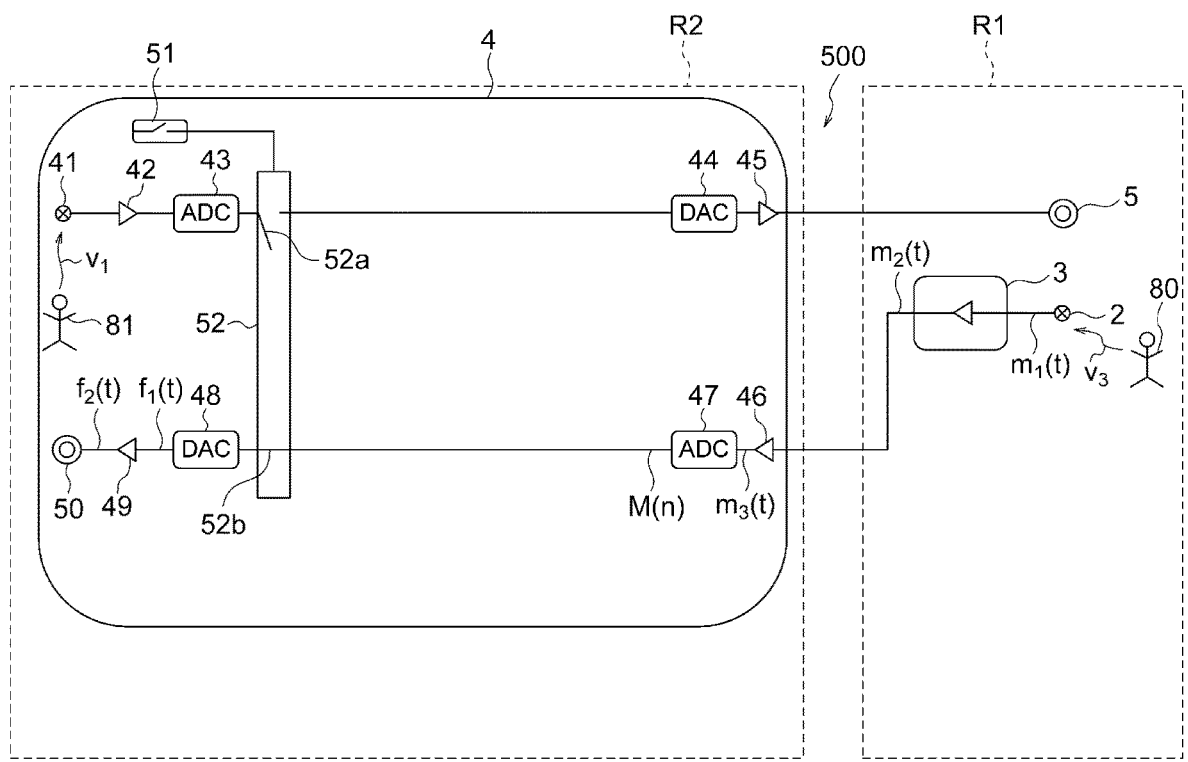
FIG. 8 is an explanatory diagram for the second communication mode.

FIG. 8 is an explanatory diagram for the second communication mode.

In the case that the operator 81 is not pressing the microphone switch 51, the switching element 52b is in an "ON" state and the switching element 52a is in an "OFF" state, as shown in FIG. 8. Accordingly, in the second communication mode, the operator microphone 41 is in a state electrically disconnected from the speaker 5 while the patient microphone 2 is in a state electrically connected to the speaker 50. Thus, in the second communication mode, when the patient 80 utters a voice, the operator 81 can hear the voice of the patient 80. In the second communication mode, the intercom module 4 operates as follows.

When the patient 80 utters a voice v3, the patient microphone 2 receives the voice v3 of the patient 80. Upon receiving the voice v3, the patient microphone 2 outputs an analog signal m1($t$) representing the received voice v3.

The amplifier board 3 receives the analog signal m1($t$) output from the patient microphone 2, amplifies the received analog signal m1($t$), and outputs an analog signal m2($t$). The amplifier board 3 amplifies the analog signal m1($t$) so that noise, if any, mixed on a signal line can be ignored.

The buffer amplifier 46 is for performing impedance conversion. Moreover, the buffer amplifier 46 adjusts the analog signal m2($t$) received from the amplifier board 3 to fall within a voltage range of the ADC 47 at the following stage, and outputs the resulting signal as an analog signal m3($t$).

The ADC 47 converts the analog signal m3($t$) output from the buffer amplifier 46 into a digital signal M(n).

Accordingly, a circuitry part constituted by the amplifier board 3, buffer amplifier 46, and ADC 47 operates as a circuitry part that generates the digital signal M(n) based on the analog signal m1($t$).

The DAC 48 converts the digital signal M(n) from the ADC 47 into an analog signal f1 ($t$).

The power amplifier 49 receives the analog signal f1($t$) from the DAC 48, amplifies the received analog signal f1($t$), and outputs an analog signal f2($t$).

The speaker 50 receives the analog signal f2($t$) from the power amplifier 49, and outputs a sound corresponding to the received analog signal f2($t$).

Accordingly, when the patient 80 utters the voice v3, the operator 81 can hear the voice v3 of the patient 80 via the speaker 50.

It can be seen from the explanation of FIGS. 7 and 8 that the intercom module 4 is in the second communication mode for transmitting the voice of the patient 80 to the operator 81 unless the operator 81 presses the microphone switch 51. Accordingly, when the patient 80 utters something, the operator 81 can hear the voice of the patient 80 from the speaker 50 while in the operation room R2. The operator 81 may continuously press the microphone switch 51 only when (s)he has to talk to the patient 80, whereby (s)he can set the intercom module 4 to the first communication mode for transmitting his/her voice to the patient 80. Having finished communicating necessary information to the patient 80, the operator 81 gets his/her hand off from the microphone switch 51. This causes the intercom module 4 to be changed from the first communication mode for transmitting the voice of the operator 81 to the patient 80 to the second communication mode for transmitting the voice of the patient 80 to the operator 81, and thus, the operator 81 can hear a response from the patient 80 via the speaker 50.

It is sometimes encountered, however, that when the operator 81 talks to the patient 80, the patient 80 does not give a prompt response. In this case, the operator 81 may be worried that the voice of the operator 81 is not output from the speaker 5 in the scan room R1 because of some problem occurring in the communication device 500. At that time, the operator 81 may talk to the patient 80 many times in order to confirm whether or not the voice of the operator 81 is being output from the speaker 5, which may disadvantageously cause unwanted work stress to the operator 81.

Moreover, there is a fear that although a voice uttered by the operator 81 is problematically not output from the speaker 5 in the scan room R1 due to, for example, a failure or the like in the communication device 500, the operator 81 is unaware of that. In this case, although the matter the operator 81 has spoken is not transmitted to the patient 80, the operator 81 may assume that the matter has been transmitted to the patient 80, and thus, the patient 80 may suffer from discomfort.

Hence, the CT apparatus 1 of the present embodiment is configured so that when uttering a voice, the operator 81 him/herself can recognize whether or not the voice of his/her own is being output from the speaker 5 in the scan room R1. Specifically, the CT apparatus 1 has a function of, when the operator 81 utters a voice, informing the operator 81 whether or not the voice of his/her own is output from the speaker 5 in the scan room R1. Now a basic configuration of the function will be described hereinbelow.

Figure 9:
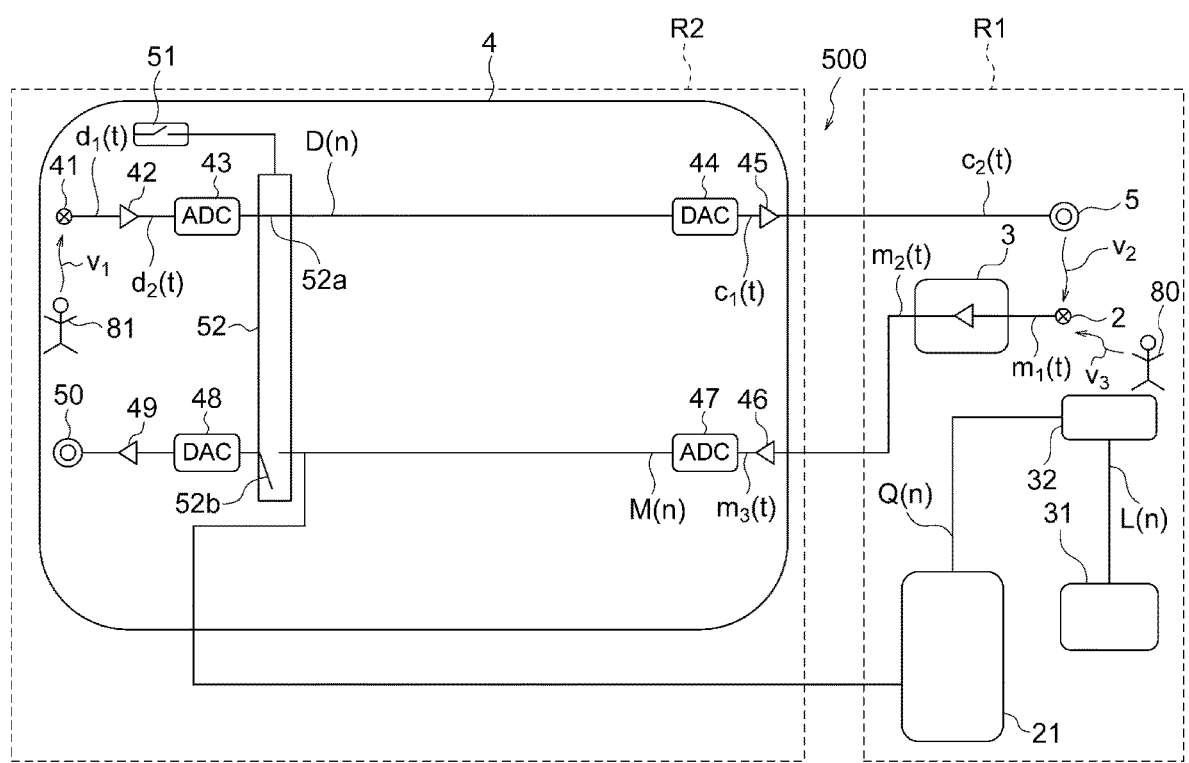
FIG. 9 is a diagram showing an example of a basic configuration of a function for informing an operator whether or not a voice of his/her own is being output from a speaker in a scan room R1.

FIG. 9 is a diagram briefly showing an example of the basic configuration of the function for informing the operator 81 whether or not the voice of his/her own is being output from the speaker 5 in the scan room R1.

To describe the basic configuration of this function, in FIG. 9 are shown the GT control section 21, light-emitting section 31, and light-emission control section 32, although not shown in FIGS. 5 to 8.

The GT control section 21 receives the digital signal M(n) output from the ADC 47. The light-emitting section 31 is connected to the GT control section 21 through the light-emission control section 32.

The light-emitting section 31 is provided on the front surface of the gantry 100, as shown in FIG. 1. The operator 81 can see the light-emitting section 31 in the gantry 100 via the window 102 while in the operation room R2. In the present embodiment, the light-emitting section 31 has a right light-emitting section 31R and a left light-emitting section 31L. The right light-emitting section 31R is provided on the right side of the bore 11, while the left light-emitting section 31L is provided on the left side of the bore 11.

Figure 10:
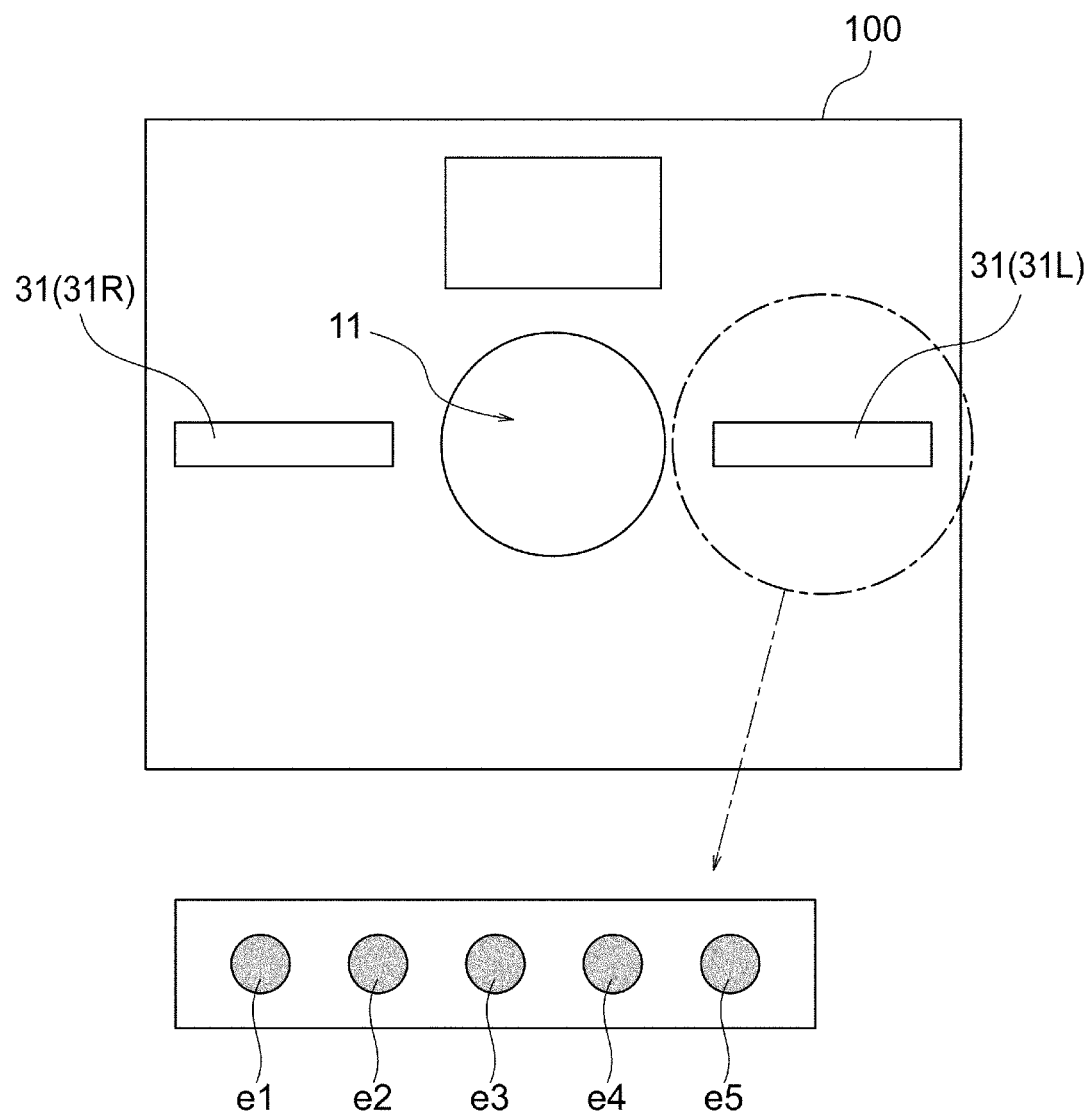
FIG. 10 is an explanatory diagram of a light-emitting section.

FIG. 10 is an explanatory diagram of the light-emitting section 31.

The light-emitting section 31 has the left light-emitting section 31L and right light-emitting section 31R. The basic structure of the left light-emitting section 31L and that of the right light-emitting section 31R are identical. Accordingly, the left one of the left light-emitting section 31L and right light-emitting section 31R will be taken here as a representative to describe the light-emitting section 31.

Referring to FIG. 10, the left light-emitting section 31L is shown in close-up. The left light-emitting section 31L comprises a plurality of light-emitting elements. While the left light-emitting section 31L having five light-emitting elements e1 to e5 is exemplified here for convenience of explanation, the number of the light-emitting elements may be less than or more than five. As the light-emitting element, an LED may be used, for example. The right light-emitting section 31R also has the same number of the light-emitting elements as that in the left light-emitting section 31L.

Returning to FIG. 9, the description will be continued.

The light-emission control section 32 controls the light-emitting section 31 to inform the operator 81 whether or not the voice of the operator 81 is being output from the speaker 5 in the scan room R1. Now a method of controlling the light-emitting section 31 will be described hereinbelow.

In FIG. 9, when the operator 81 utters the voice v1, the voice v2 of the operator 81 is output from the speaker 5, as described earlier with reference to FIG. 7.

The patient microphone 2 receives the voice v2 of the operator 81 output from the speaker 5. Upon receiving the voice v2, the patient microphone 2 outputs the analog signal m1(t) representing the received voice v2. The amplifier board 3 processes the analog signal m1(t) to output the analog signal m2(t). The analog signal m2(t) is processed by the buffer amplifier 46, and the analog signal m3(t) output from the buffer amplifier 46 is converted into the digital signal M(n) by the ADC 47. While the digital signal M(n) is output toward the DAC 48, it is not supplied to the DAC 48 because the switching element 52b at the previous stage of the DAC 48 is "OFF."

However, since the ADC 47 is connected to the GT control section 21, the digital signal M(n) is supplied to the GT control section 21.

The GT control section 21 converts the digital signal M(n) into a digital signal Q(n) compatible with a CAN (Controller Area Network) communication, and outputs the digital signal Q(n) to the light-emission control section 32.

The light-emission control section 32 outputs a control signal L(n) to the light-emitting section 31 based on the digital signal Q(n), for energizing the light-emitting section 31 depending upon the loudness of the voice of the operator 81.

Now a method of energizing the light-emitting section 31 depending upon the loudness of the voice of the operator 81 will be described hereinbelow with reference to FIGS. 11 to 16.

Figure 11:
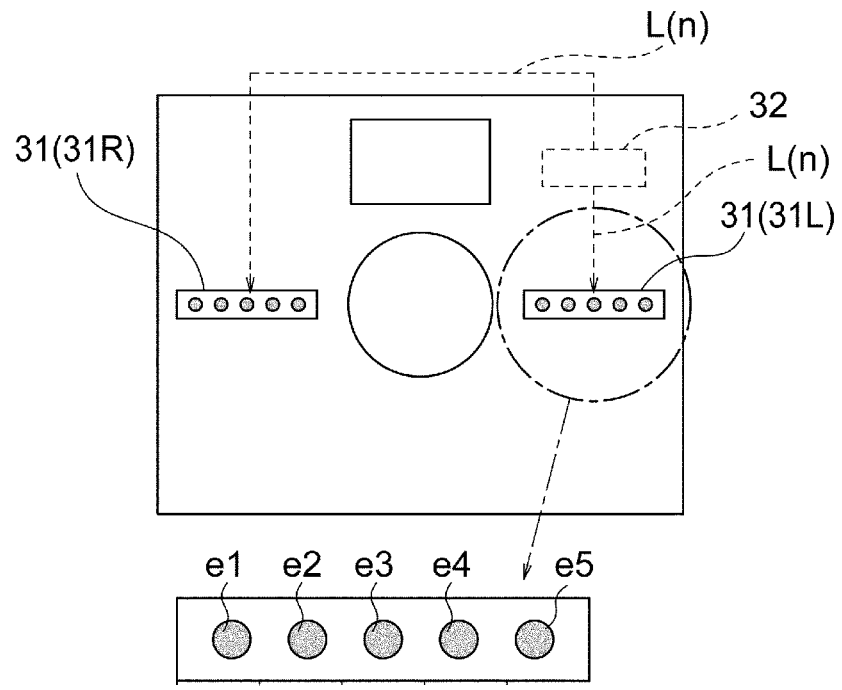
FIG. 11 is an explanatory diagram of the light-emitting section in $t0 \leq t < t1$.
Figure 11:
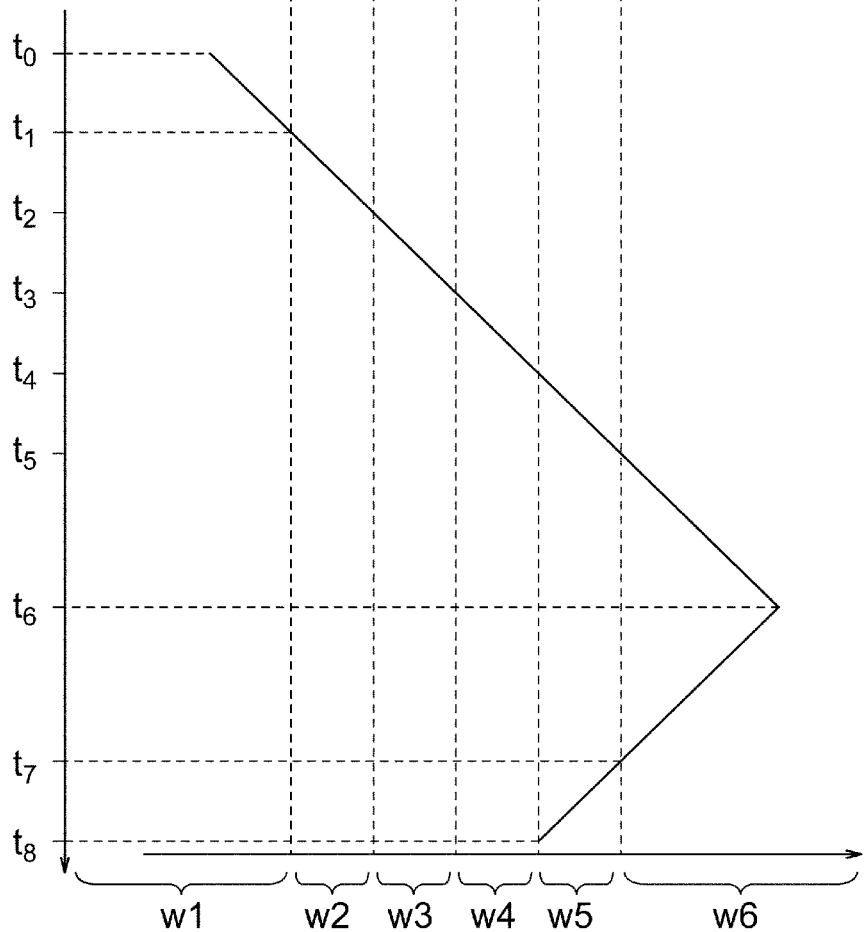

FIG. 11 shows in its lower portion a waveform of the voice of the operator 81 between time points t0 and t8. A vertical axis represents the time, and a horizontal axis represents the loudness of the voice of the operator 81. Although the voice waveform changes with time in a complex manner in practice, it is shown as a simple waveform in FIG. 11 to facilitate understanding of the operation of the light-emitting section 31. Here, the loudness of the voice is assumed to linearly increase with time from time point t0 to point t6 and linearly decrease with time from time point t6 to point t8.

The light-emission control section 32 identifies which of regions w1 to w6 the loudness of the voice at a time point t falls within. The light-emission control section 32 then determines those to be energized and those not to be energized among the light-emitting elements (LED) e1 to e5 depending upon which region the loudness of the voice falls within.

In the present embodiment, the light-emitting elements to be energized and those not to be energized are determined following (1) to (6) below.

(1) In the case that the loudness of the voice falls within the region w1, it is determined that the light-emitting elements to be energized do not exist, i.e., no light-emitting element is energized.

(2) In the case that the loudness of the voice falls within the region w2, it is determined that the light-emitting element e1 is energized and the other light-emitting elements e2 to e5 are not energized.

(3) In the case that the loudness of the voice falls within the region w3, it is determined that the light-emitting elements e1 and e2 are energized and the other light-emitting elements e3 to e5 are not energized.

(4) In the case that the loudness of the voice falls within the region w4, it is determined that the light-emitting elements e1, e2, and e3 are energized and the other light-emitting elements e4 and e5 are not energized.

(5) In the case that the loudness of the voice falls within the region w5, it is determined that the light-emitting elements e1 to e4 are energized and the other light-emitting element e5 is not energized.

(6) In the case that the loudness of the voice falls within the region w6, it is determined that all the light-emitting elements e1 to e5 are energized.

Now which one(s) of the light-emitting elements e1 to e5 is/are energized at each time point t will be described hereinbelow.

In $t0 \leq t < t1$, the light-emission control section 32 decides that the loudness of the voice falls within the region w1. Accordingly, the light-emission control section 32 outputs the control signal L(n) not to energize any of the light-emitting elements (LEDs) e1 to e5 following (1) above. Accordingly, no light-emitting elements e1 to e5 emit light in $t0 \leq t < t1$.

Figure 12:
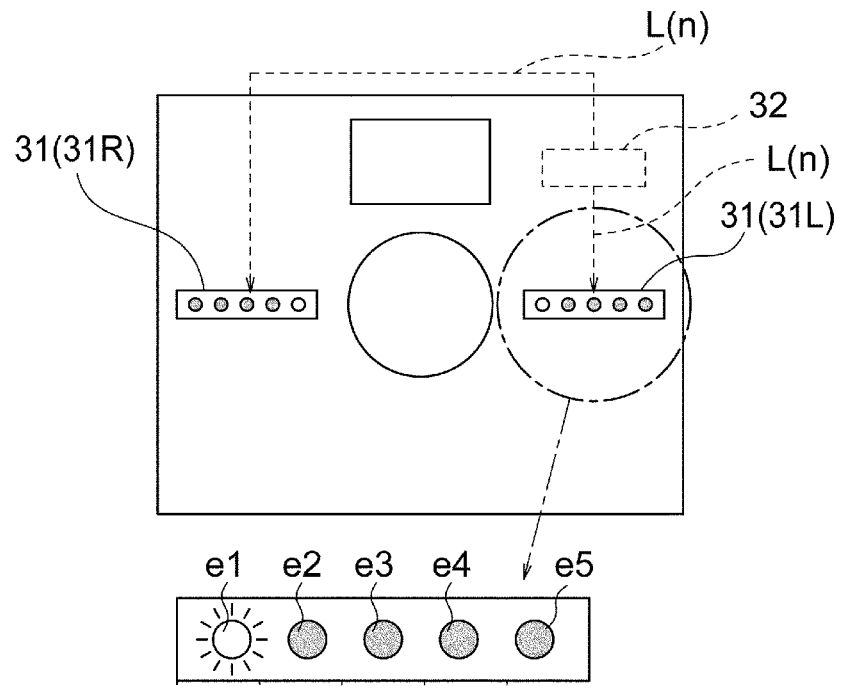
FIG. 12 is an explanatory diagram of the light-emitting section in $t1 \leq t < t2$.
Figure 12:
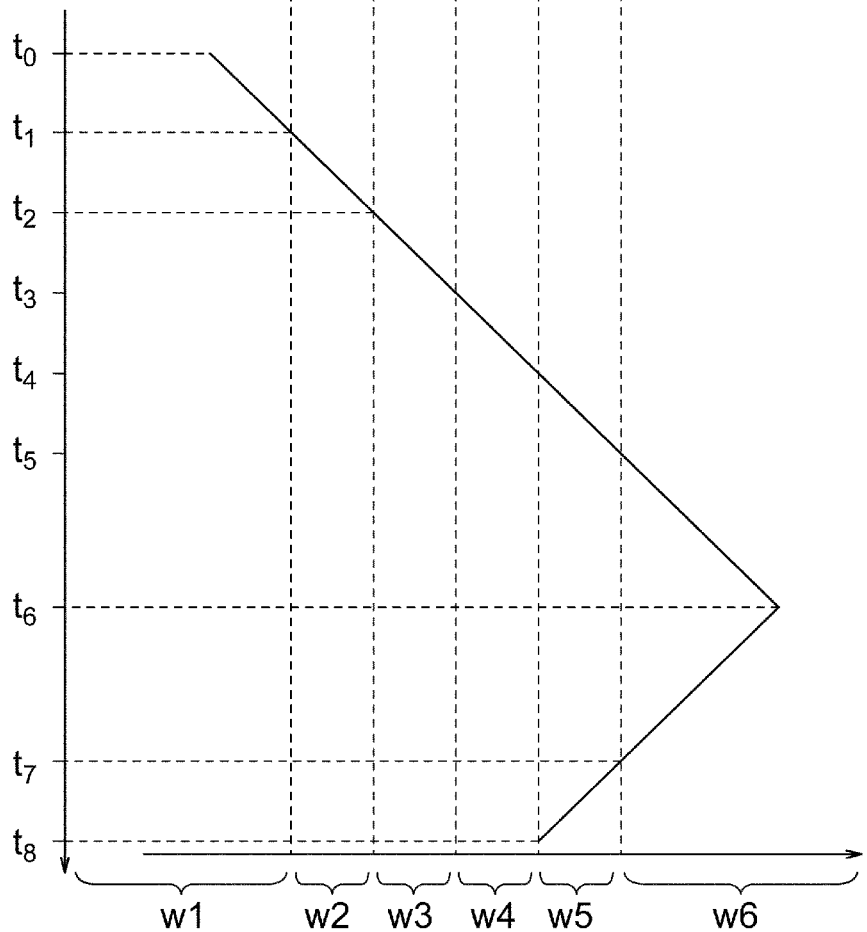

FIG. 12 is an explanatory diagram of the light-emitting section 31 in $t1 \leq t < t2$.

In $t1 \leq t < t2$, the light-emission control section 32 decides that the loudness of the voice falls within the region w2. Accordingly, the light-emission control section 32 outputs the control signal L(n) to energize the light-emitting element e1 and not to energize the other light-emitting elements e2 to e5 following (2) above. Accordingly, only the light-emitting element e1 among the light-emitting elements e1 to e5 emits light in $t1 \leq t < t2$.

Figure 13:
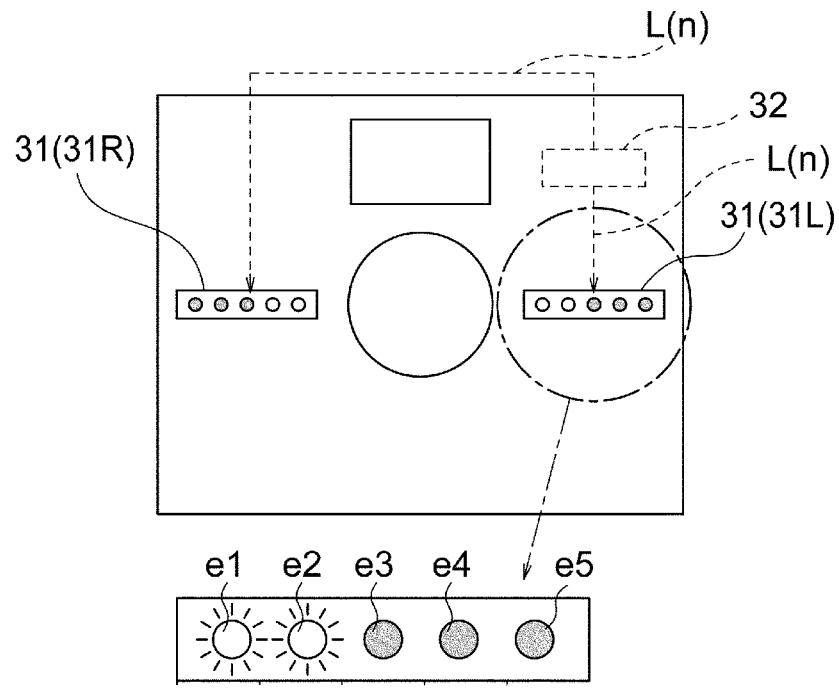
FIG. 13 is an explanatory diagram of the light-emitting section in $t2 \leq t < t3$.
Figure 13:
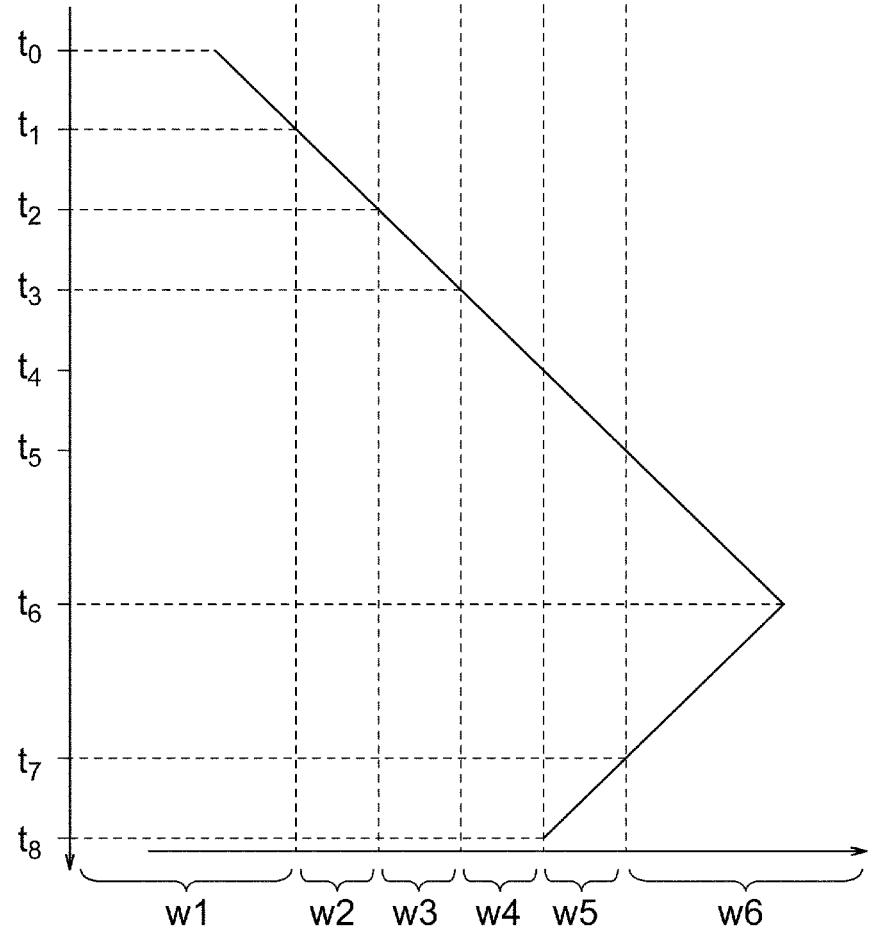

FIG. 13 is an explanatory diagram of the light-emitting section 31 in $t2 \leq t < t3$.

In $t2 \leq t < t3$, the light-emission control section 32 decides that the loudness of the voice falls within the region w3. Accordingly, the light-emission control section 32 outputs the control signal L(n) to energize the light-emitting elements e1 and e2 and not to energize the other light-emitting elements e3 to e5 following (3) above. Accordingly, the light-emitting elements e1 and e2 among the light-emitting elements e1 to e5 emit light in $t2 \leq t < t3$.

Figure 14:
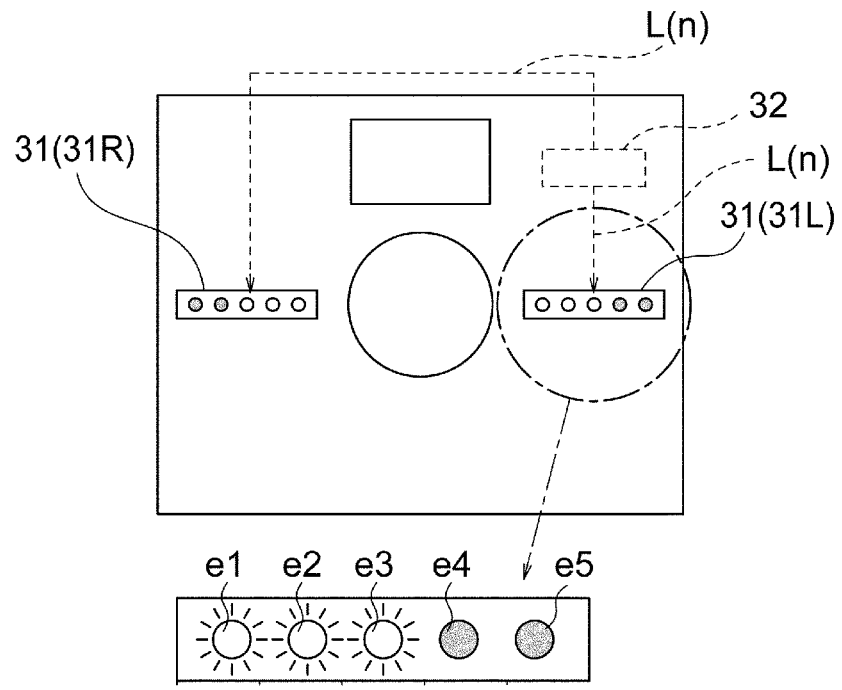
FIG. 14 is an explanatory diagram of the light-emitting section in $t3 \leq t < t4$.
Figure 14:
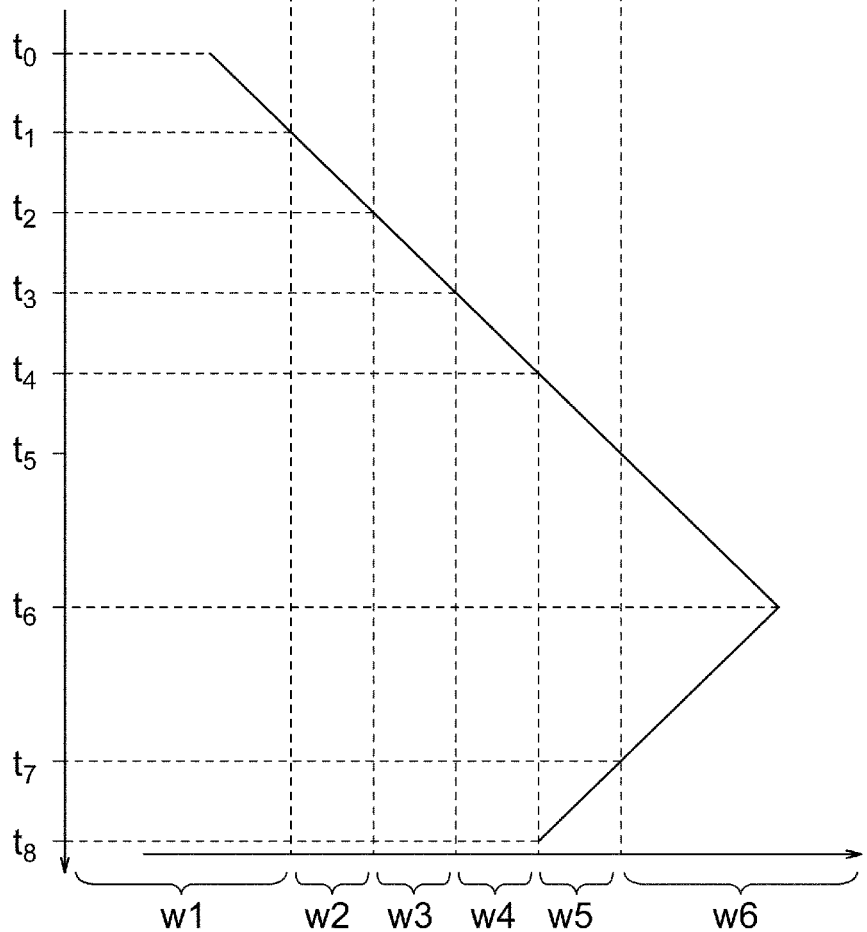

FIG. 14 is an explanatory diagram of the light-emitting section 31 in $t3 \leq t < t4$.

In $t3 \leq t < t4$, the light-emission control section 32 decides that the loudness of the voice falls within the region w4. Accordingly, the light-emission control section 32 outputs the control signal L(n) to energize the light-emitting elements e1, e2, and e3 and not to energize the other light-emitting elements e4 and e5 following (4) above. Accordingly, the light-emitting elements e1, e2, and e3 among the light-emitting elements e1 to e5 emit light in $t3 \leq t < t4$.

Figure 15:
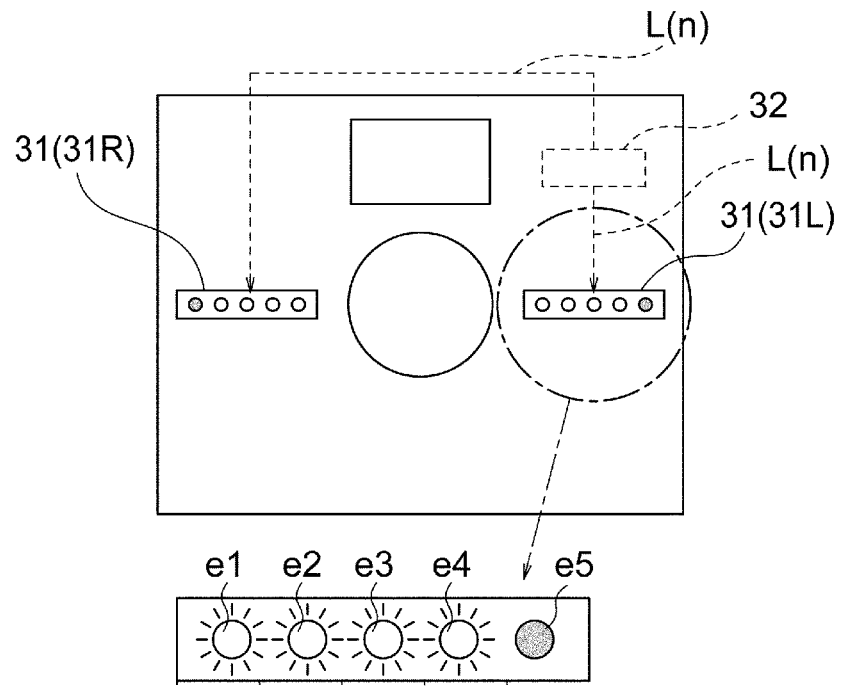
FIG. 15 is an explanatory diagram of the light-emitting section in $t4 \leq t < t5$.
Figure 15:
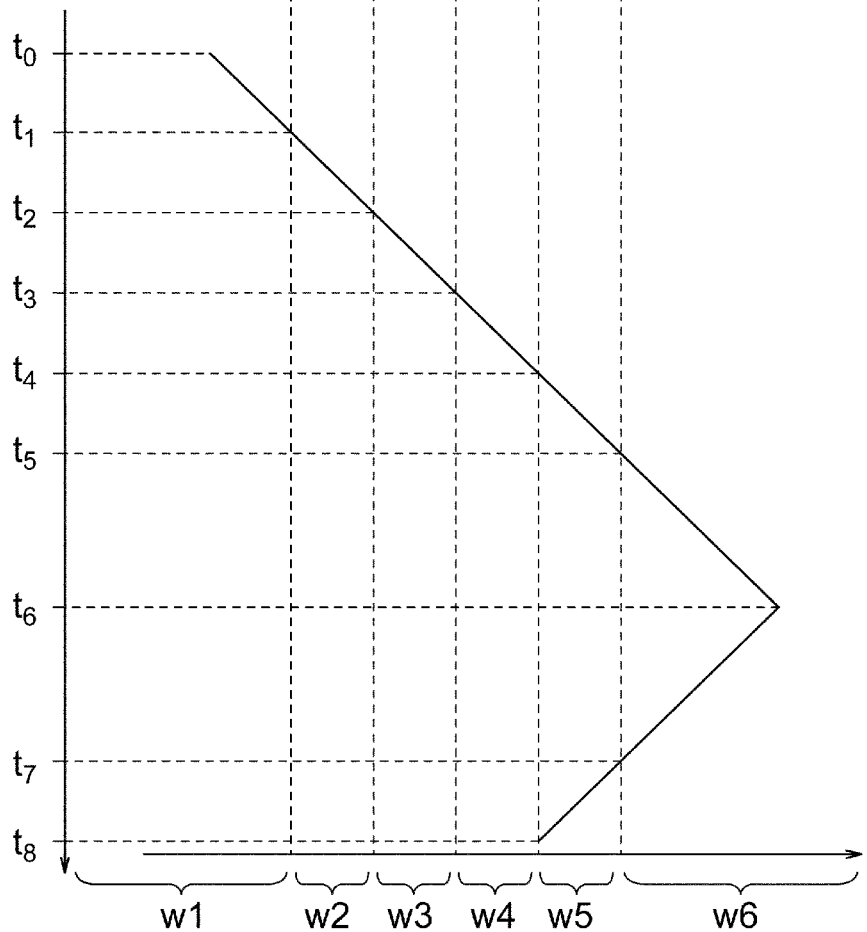

FIG. 15 is an explanatory diagram of the light-emitting section 31 in $t4 \leq t < t5$.

In $t4 \leq t < t5$, the light-emission control section 32 decides that the loudness of the voice falls within the region w5. Accordingly, the light-emission control section 32 outputs the control signal L(n) to energize the light-emitting elements e1, e2, e3, and e4 and not to energize the other light-emitting element e5 following (5) above. Accordingly, the light-emitting elements e1, e2, e3, and e4 among the light-emitting elements e1 to e5 emit light in $t4 \leq t < t5$.

Figure 16:
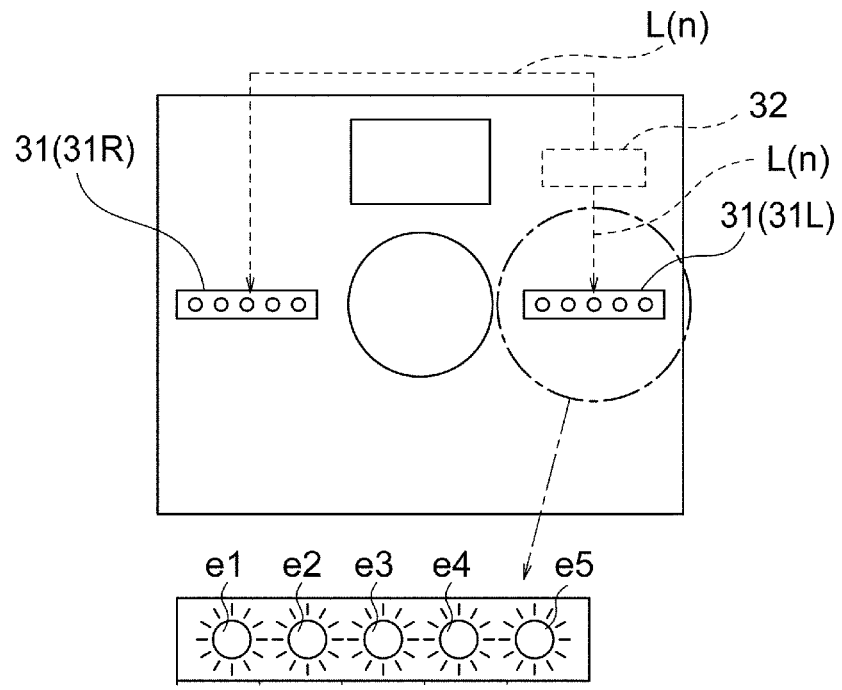
FIG. 16 is an explanatory diagram of the light-emitting section in $t5 \leq t < t7$.
Figure 16:
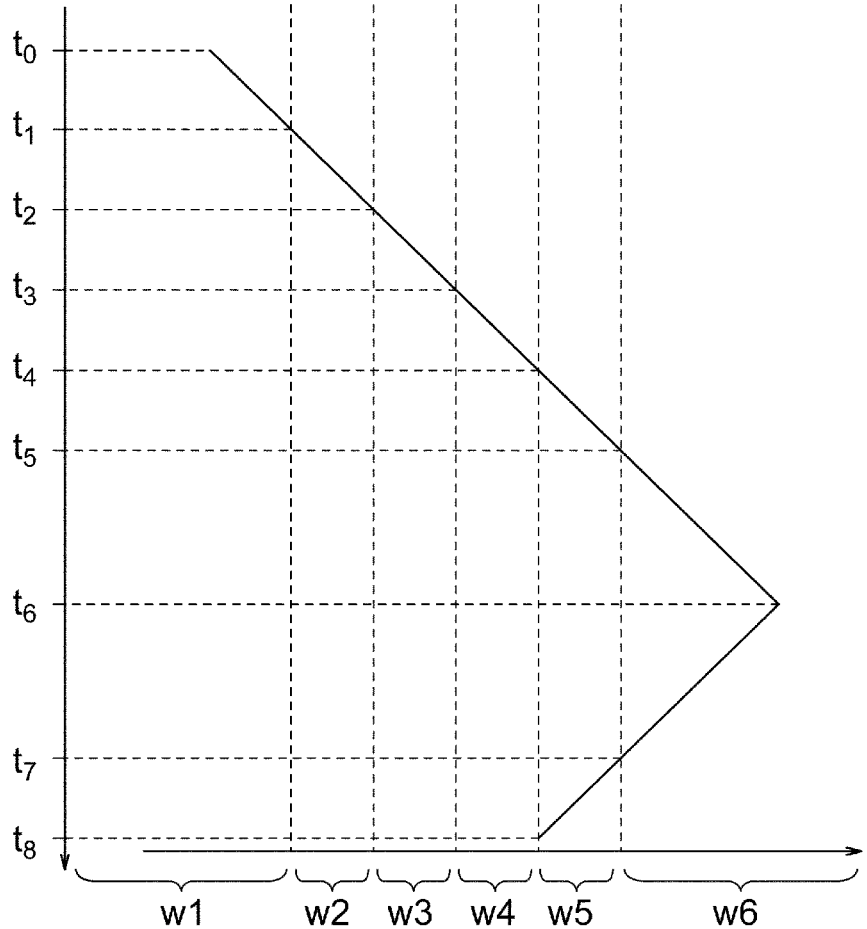

FIG. 16 is an explanatory diagram of the light-emitting section 31 in $t5 \leq t < t7$.

In $t5 \leq t < t7$, the light-emission control section 32 decides that the loudness of the voice falls within the region w6. Accordingly, the light-emission control section 32 outputs the control signal L(n) to energize all the light-emitting elements e1 to e5 following (6) above. Accordingly, all the light-emitting elements e1 to e5 emit light in $t5 \leq t < t7$.

In $t7 \leq t < t8$, the loudness of the voice falls within the region w5, as in $t4 \leq t < t5$, and therefore, the light-emitting elements e1, e2, e3, and e4 among the light-emitting elements e1 to e5 emit light, as shown in FIG. 15.

Accordingly, in the case that the loudness of the voice of the operator 81 exceeds a threshold between the regions w1 and w2, the light-emitting section 31 emits light, and therefore, the operator 81 can see the light-emitting section 31 while uttering a voice to thereby visually confirm whether or not the voice of the operator 81 is being output from the speaker 5 (see FIG. 1).

Moreover, when the operator 81 utters a voice, the number of energized light-emitting elements changes depending upon the loudness of the voice. In the present embodiment, the number of energized light-emitting elements increases as the loudness of the voice increases. For example, in the case that the voice waveform changes as shown in FIGS. 11 to 16, the number of energized light-emitting elements is incremented by one with time in $t0 \leq t < t7$. On the other hand, the number of energized light-emitting elements decreases as the loudness of the voice decreases. For example, in $t7 \leq t < t8$, the number of energized light-emitting elements is decremented by one. Accordingly, the light-emitting section 31 functions as a level meter in which the number of energized light-emitting elements increases or decreases depending upon the loudness of the voice of the operator 81, and thus, volume information indicating the loudness of the voice of the operator 81 can be given to the operator 81. Therefore, the operator 81 can see the light-emitting section 31 while uttering a voice to thereby visually recognize at how much loudness the voice of the operator 81 is heard by the patient 80.

Moreover, to avoid a situation in which the voice of the operator 81 is so low that the patient 80 is unaware of the voice of the operator 81, the light-emitting section 31 is set not to emit light in the case that the loudness of the voice that the operator 81 has uttered is lower than the threshold between the regions w1 and w2. Accordingly, in the case that the light-emitting section 31 emit no light in spite of the fact that the operator 81 utters a voice, the operator 81 can become aware that the voice of his/her own may be too low, and therefore, the operator 81 can immediately utter the voice again so as to be heard by the patient 80.

Sometimes the patient 80 may utter the voice v3 (see FIG. 9) while the intercom module 4 is set to the first communication mode. In this case, since the patient 80 utters the voice v3 when the operator 81 does not utter the voice v1, the patient microphone 2 receives the voice v3 of the patient 80. However, the light-emitting section 31 emitting light in response to the voice v3 of the patient 80 received by the patient microphone 2 in spite of the fact that the operator 81 does not utter the voice v1, may confuse the operator 81. Moreover, in CT imaging the patient 80, the operation of machinery, such as the gantry 100 and/or table 200, generates operating noise, and furthermore, another operator, if any, in the scan room R1, may utter a voice. Again, in these cases, the light-emitting section 31 emitting light in response to the operating noise from machinery or the voice of the operator in the scan room R1, may confuse the operator 81.

Hence, the CT apparatus 1 in the present embodiment has a filter block for energizing the light-emitting section 31 in response only to the voice of the operator 81 even when a sound (e.g., the voice of the patient 80, operating noise from machinery, and/or voice of the operator in the scan room R1) other than the voice of the operator 81 is generated while the intercom module 4 is set to the first communication mode. Now the filter block will be described hereinbelow.

Figure 17:
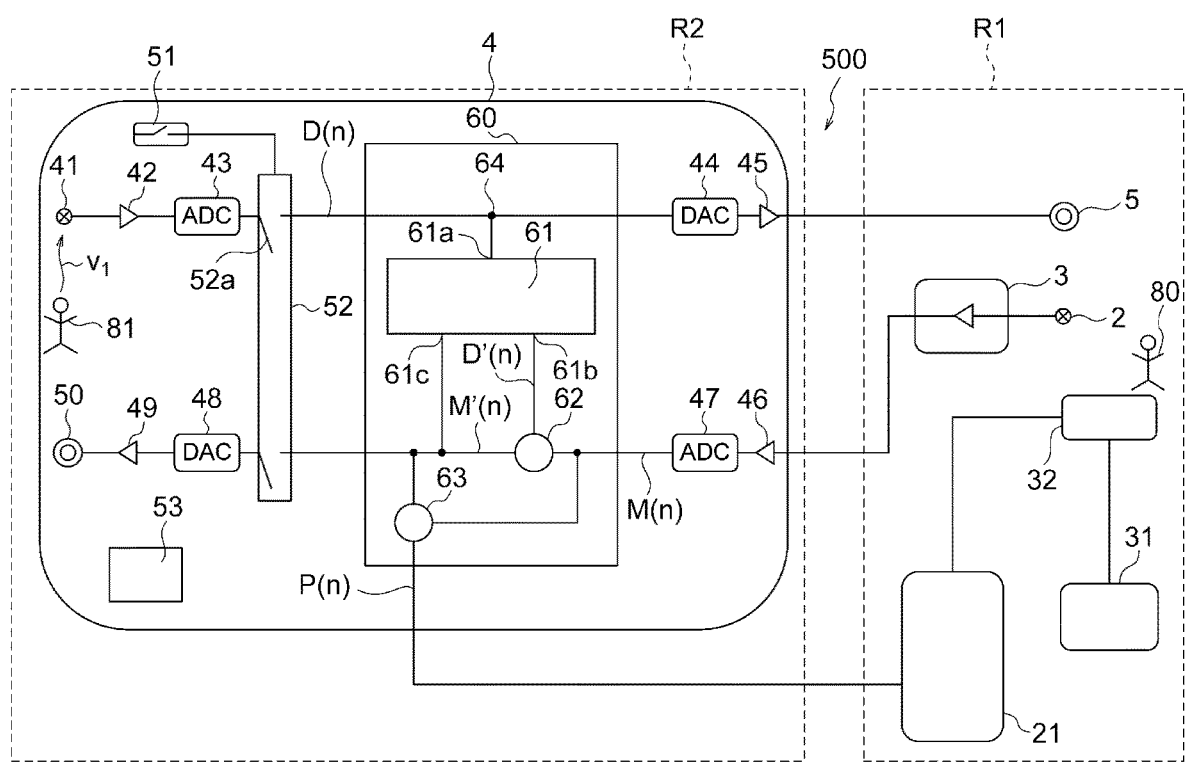
FIG. 17 is an explanatory diagram of a filter block.

FIG. 17 is an explanatory diagram of the filter block.

The intercom module 4 has a filter block 60. The filter block 60 is constructed from a DSP (Digital Signal Processor). The filter block 60 has an adaptive filter 61, a subtracting section 62, and a subtracting section 63.

The adaptive filter 61 has an input section 61a connected to a node 64 between the switching element 52a and DAC 44. The digital signal D(n) output from the ADC 43 is input to the input section 61a of the adaptive filter 61.

The subtracting section 62 is connected to an output section 61b of the adaptive filter 61 and to the ADC 47. The subtracting section 62 receives the digital signal M(n) from the ADC 47 and a digital signal D'(n) from the adaptive filter 61, subtracts the digital signal D'(n) from the digital signal M(n), and outputs a digital signal M'(n) resulting from the subtraction.

Moreover, the adaptive filter 61 has an input section 61c for receiving the digital signal M'(n) output from the subtracting section 62. The adaptive filter 61 adjusts its coefficients based on the digital signal M'(n) so that a difference between the digital signal D(n) received at the input section 61a and the digital signal D'(n) output from the output section 61b is as close to zero as possible.

The subtracting section 63 receives the digital signal M'(n) output from the subtracting section 62 and also receives the digital signal M(n) output from the ADC 47. The subtracting section 63 subtracts the digital signal M'(n) from the digital signal M(n), and outputs a digital signal P(n) resulting from the subtraction.

The filter block 60 is thus configured as described above.

Next, an operation of the intercom module 4 provided with the filter block 60 will be described separately for the first communication mode and for the second communication mode.

Figure 18:
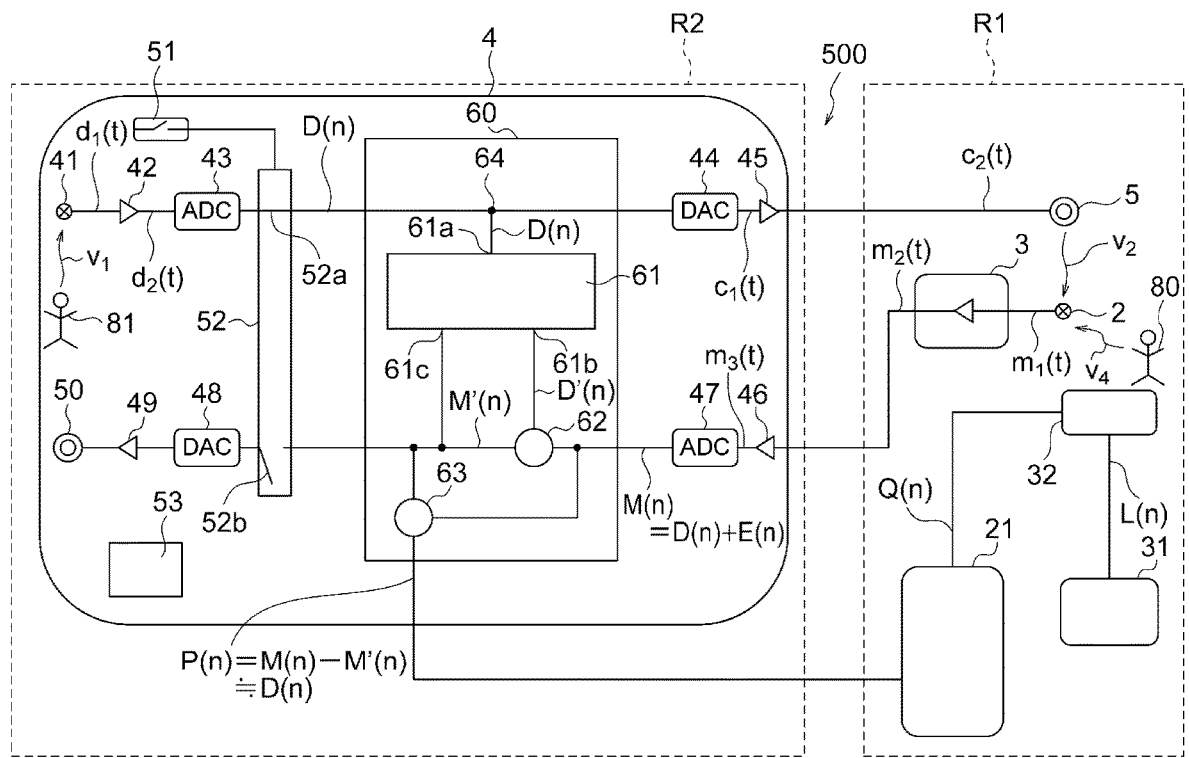
FIG. 18 is an explanatory diagram for an operation of the intercom module in the first communication mode.

FIG. 18 is an explanatory diagram for an operation of the intercom module 4 in the first communication mode.

To set the intercom module 4 to the first communication mode, the operator 81 continuously presses the microphone switch 51. As shown in FIG. 18, the switching element 52a is set to "ON" and the switching element 52b is set to "OFF" while the operator 81 is pressing the microphone switch 51. Accordingly, in the first communication mode, the patient microphone 2 is set to a state electrically disconnected from the speaker 50, while the operator microphone 41 is in a state electrically connected to the speaker 5.

When the operator 81 utters the voice v1, the operator microphone 41 receives the voice v1 of the operator 81. Upon receiving the voice v1, the operator microphone 41 outputs the analog signal d1(t) representing the received voice v1. The preamplifier 42 receives the analog signal d1(t), amplifies the analog signal d1 (t), and outputs the analog signal d2(t).

The ADC 43 converts the analog signal d2(t) into the digital signal D(n). The digital signal D(n) is a signal containing sound data representing the sound that the operator microphone 41 has received (the voice v1 of the operator 81 here). The digital signal D(n) is supplied to the DAC 44.

The DAC 44 converts the digital signal D(n) into the analog signal c1 (t). The power amplifier 45 receives the analog signal c1 (t), and outputs the analog signal c2(t). The analog signal c2(t) is input to the speaker 5, which in turn outputs the voice v2 of the operator 81 corresponding to the received analog signal c2(t).

The operation described above is identical to that described with reference to FIG. 9, where the filter block 60 is omitted in the drawing. However, since the CT apparatus 1 comprises the filter block 60 as shown in FIG. 18, the digital signal D(n) is supplied to the filter block 60, in addition to the DAC 44. In the case that the sound received by the patient microphone 2 contains the voice v2 (voice of the operator 81 output from the speaker 5), and in addition, another sound v4 (e.g., the voice of the patient 80, operating noise from machinery, and/or voice of the operator in the scan room R1), the filter block 60 executes processing of removing the sound v4 from a sound (v2+v4) received by the patient microphone 2. Now the processing will be particularly described hereinbelow.

As shown in FIG. 18, the patient microphone 2 receives the voice v2 of the operator 81 output from the speaker 5, and in addition, another sound v4 (e.g., including the voice of the patient 80, operating noise from machinery, and/or the voice of the operator in the scan room R1). The sound v4 will be referred to hereinbelow as noise. Upon receiving the sound containing the voice v2 of the operator 81 and noise v4, the patient microphone 2 outputs an analog signal m1(t) representing the received sound.

The analog signal m1(t) is input to the amplifier board 3. The amplifier board 3 processes the analog signal m1(t), and outputs an analog signal m2(t). The buffer amplifier 46 processes the analog signal m2(t), and outputs an analog signal m3(t). The analog signal m3(t) may be expressed by the following equation:

$$m3(t)=d3(t)+e(t) \tag{1}$$

wherein the signal component d3(t) is a signal component corresponding to the voice v2 of the operator 81 output from the speaker 5, and the signal component e(t) is a signal component corresponding to the noise v4.

The analog signal m3(t) is converted into a digital signal M(n) at the ADC 47. The digital signal M(n) is a signal containing sound data representing the sound (sound containing the voice v2 and noise v4 here) that the patient microphone 2 has received. The digital signal M(n) may be expressed by the following equation:

$$M(n)=D3(n)+E(n) \tag{2}$$

wherein D3(n) and E(n) correspond, respectively, to the signal components d3(t) and e(t) of the analog signal m3(t) input to the ADC 47 (see the right side of EQ. (1)). Accordingly, the signal component D3(n) of the digital signal M(n) represents the signal component corresponding to the voice v2 of the operator 81 output from the speaker 5, and the signal component E(n) of the digital signal M(n) represents the signal component E(n) corresponding to the noise v4.

Comparing the signal component D3(n) with the digital signal D(n) described earlier, the signal component D3(n) represents the voice v2 received by the patient microphone 2 in the scan room R1, while the digital signal D(n) represents the voice v1 received by the operator microphone 41 in the operation room R2. Since the voice v2 may be considered to be substantially the same as the voice v1, the signal component D3(n) may be considered to be substantially the same as the digital signal D(n). Hence, representing D3(n)=D(n), EQ. (2) may be expressed by the following equation:

$$\begin{aligned} M(n) &= D3(n) + E(n) \\ &= D(n) + E(n) \end{aligned} \tag{3}$$

Accordingly, in the present embodiment, the digital signal M(n) is considered to be expressed by a sum of the two signal components D(n) and E(n), as given by EQ. (3).

The digital signal M(n) is supplied to the subtracting section 62.

Moreover, as described earlier, the filter block 60 has the adaptive filter 61. The adaptive filter 61 receives the digital signal D(n), and outputs the digital signal D'(n). The digital signal D'(n) is output to the subtracting section 62.

The subtracting section 62 subtracts the digital signal D'(n) that the adaptive filter 61 has output, from the digital signal M(n) that the ADC 47 has output, and outputs a digital signal M'(n). The digital signal M'(n) may be expressed by the following equation:

$$M'(n)=M(n)-D'(n) \quad (4)$$

Substituting M(n) expressed by EQ. (3) into EQ. (4), the following equation results:

$$M'(n) = M(n) - D'(n) \quad (5)$$
$$= D(n) + E(n) - D'(n)$$

As described earlier, the adaptive filter 61 receives the digital signal M'(n) from the subtracting section 62 via the input section 61c. The adaptive filter 61 adjusts its coefficients based on the digital signal M'(n) received from the subtracting section 62 so that a difference between the digital signal D(n) received at the input section 61a and the digital signal D'(n) output from the output section 61b is as close to zero as possible. This allows us to regard D'(n) as D'(n)≈D(n). Thus, EQ. (5) may be expressed by the following equation:

$$M'(n) = D(n) + E(n) - D'(n) \quad (6)$$
$$\approx E(n)$$

As described earlier, E(n) represents the signal component corresponding to the noise v4. Accordingly, by the subtracting section 62 subtracting the digital signal D'(n) that the adaptive filter 61 has output, from the digital signal M(n) that the ADC 47 has output, the digital signal M'(n) representing the signal component corresponding to the noise v4 can be generated from the digital signal M(n).

The filter block 60 also has another subtracting section 63. The subtracting section 63 subtracts the digital signal M'(n) from the digital signal M(n) that the ADC 47 has output, and outputs a digital signal P(n). The digital signal P(n) is expressed by the following equation:

$$P(n)=M(n)-M'(n) \quad (7)$$

wherein M(n) is expressed by EQ. (3), and M'(n) is expressed by EQ. (6); therefore, EQ. (7) may be changed into the following equation:

$$P(n) = M(n) - M'(n) \quad (8)$$
$$\approx D(n) + E(n) - E(n)$$
$$\approx D(n)$$

As given by EQ. (6), the digital signal M'(n) represents the signal component E(n) substantially corresponding to the noise v4. Accordingly, by the subtracting section 63 subtracting the digital signal M'(n) from the digital signal M(n), a digital signal P(n)≈D(n) containing sound data representing the voice v2 of the operator can be generated.

In this way, the filter block 60 can remove signal components substantially corresponding to the noise v4 from the digital signal M(n) containing the voice v2 of the operator and noise v4 to extract the digital signal P(n)≈D(n) corresponding to the voice v2 of the operator.

The digital signal P(n)≈D(n) output from the filter block 60 is input to the GT control section 21.

The GT control section 21 executes processing of converting the digital signal P(n)≈D(n) into a digital signal Q(n) compatible with a CAN (Controller Area Network) communication. The GT control section 21 has a storage section storing therein a program for executing the processing of converting the digital signal P(n) into the digital signal Q(n) compatible with a CAN communication, and a processor for loading the program stored in the storage section and executing the conversion processing. The storage section in the GT control section 21 may be a non-transitory, computer-readable recording medium storing therein one or more processor-executable instructions. The one or more instructions, when executed by the processor, causes the processor to execute the operation of converting the digital signal P(n) into the digital signal Q(n).

The GT control section 21 outputs the digital signal Q(n) to the light-emission control section 32.

The light-emission control section 32 executes processing of controlling the light-emitting section 31 based on the digital signal Q(n). The light-emission control section 3 has a storage section storing therein a program for controlling the light-emitting section 31 based on the digital signal Q(n), and a processor for loading the program stored in the storage section and executing the control processing. The storage section in the light-emission control section 32 may be a non-transitory, computer-readable recording medium storing therein one or more processor-executable instructions. The one or more instructions, when executed by the processor, causes the processor to execute the operation of controlling the light-emitting section 31 based on the digital signal Q(n).

As described earlier with reference to FIGS. 11 to 16, the light-emitting section 31 changes the number of energized light-emitting elements depending upon the loudness of the voice of the operator 81.

As described above, when noise v4 occurs in the first communication mode, the patient microphone 2 receives the voice v2 of the patient 80, and in addition, the noise v4. However, since the operation of the filter block 60 can remove the noise v4 from the sound (v2+v4) received by the patient microphone 2, the GT control section 21 is supplied with the digital signal P(n) containing substantially only the voice of the operator 81. Accordingly, even when the noise v4 occurs in the first communication mode, the light-emitting section 31 can be energized in response to the loudness of the voice of the operator 81.

The main operations of the adaptive filter 61, and subtracting sections 62 and 63 in the first communication mode shown in FIG. 18 are as follows.

(a1) The input section 61a of the adaptive filter 61 receives the digital signal D(n) containing sound data representing a sound that the operator microphone 41 has received.

(a2) The subtracting section 62 receives the digital signal M(n) containing sound data representing a sound that the patient microphone 2 has received.

(a3) The subtracting section 62 generates the digital signal M'(n) representing signal components corresponding to the noise v4 from the digital signal M(n).

(a4) The adaptive filter 61 generates the digital signal D'(n) based on the digital signal D(n) and digital signal M'(n). The adaptive filter 61 also adjusts its coefficients based on the digital signal M'(n) so that a difference between the digital signal D(n) and digital signal D'(n) is as close to zero as possible.

(a5) The subtracting section 63 subtracts the digital signal M'(n) from the digital signal M(n) to thereby generate the digital signal P(n) containing sound data representing the voice of the operator 81.

Moreover, the intercom module 4 has a storage section 53 storing therein a program for executing the processing of the filter block 60 described above with reference to FIG. 18. The filter block 60 is configured as a processor for loading the program stored in the storage section 53 and executing the processing. The storage section 53 may be a non-transitory, computer-readable recording medium storing therein one or more processor-executable instructions. The one or more instructions, when executed by the processor, causes the processor to execute the operations comprising the processing of (b1)-(b5) below:

(b1) receiving the digital signal D(n) containing sound data representing a sound that the operator microphone 41 has received;

(b2) receiving the digital signal M(n) containing sound data representing a sound that the patient microphone 2 has received;

(b3) generating the digital signal M'(n) representing signal components corresponding to noise from the digital signal M(n);

(b4) generating the digital signal D'(n) based on the digital signal D(n) and digital signal M'(n); and (b5) subtracting the digital signal M'(n) from the digital signal D(n) to thereby generate the digital signal P(n) containing sound data representing the voice of the operator 81.

In the present embodiment, the program for executing the operations comprising the processing (b1)-(b5) above is stored in the storage section 53 of the intercom module 4. The program, however, may be stored in a storage section different from the storage section 53, or only part of the program may be stored in a storage section different from the storage section 53.

In FIG. 18, the operation of the CT apparatus 1 in the first communication mode is described. Next, the operation of the CT apparatus 1 in the second communication mode will be described hereinbelow.

Figure 19:
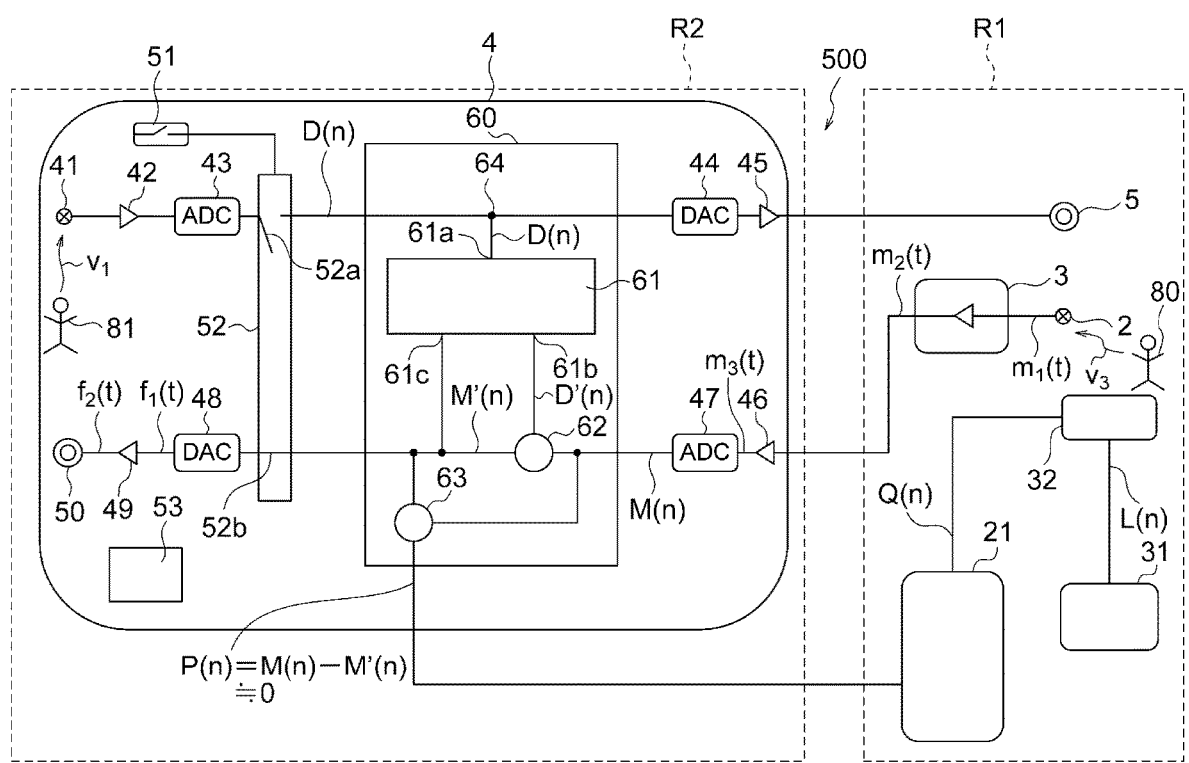
FIG. 19 is an explanatory diagram for an operation of the intercom module in the second communication mode.

FIG. 19 is an explanatory diagram for an operation of the intercom module 4 in the second communication mode.

When the operator 81 is not pressing the microphone switch 51, the switching element 52b is in an "ON" state and the switching element 52a is in an "OFF" state, as shown in FIG. 19. Accordingly, in the second communication mode, the operator microphone 41 is in a state electrically disconnected from the speaker 5 while the patient microphone 2 is in a state electrically connected to the speaker 50.

When the patient 80 utters the voice v3, the patient microphone 2 receives the voice v3 of the patient 80. Upon receiving the voice v3, the patient microphone 2 outputs the analog signal m1(t) representing the received voice v3.

The amplifier board 3 receives the analog signal m1(t) output from the patient microphone 2, amplifies the received analog signal m1(t), and outputs the analog signal m2(t). The buffer amplifier 46 processes the analog signal m2(t) received from the amplifier board 3, and outputs the analog signal m3(t).

The ADC 47 converts the analog signal m3(t) output from the buffer amplifier 46 into the digital signal M(n).

The digital signal M(n) is supplied to the subtracting section 62.

The subtracting section 62 subtracts the digital signal D'(n) that the adaptive filter 61 has output, from the digital signal M(n) that the ADC 47 has output, and outputs the digital signal M'(n). The digital signal M'(n) may be expressed by the following equation:

$$M'(n) = M(n) - D'(n) \tag{9}$$

In the second communication mode, the switching element 52a is "OFF," and this allows us to regard the digital signal D'(n) as D'(n)≈0. Accordingly, EQ. (9) may be expressed by the following equation:

$$M'(n) = M(n) - D'(n) \tag{10}$$
$$\approx M(n)$$

Since the digital signal M(n) represents the voice v3 of the patient 80, it can be seen that the digital signal M'(n) output by the subtracting section 62 substantially represents the voice v3 of the patient 80.

The digital signal M'(n) is input to the DAC 48. The DAC 48 converts the digital signal M'(n) into the analog signal f1(t). The power amplifier 49 receives the analog signal f1(t) from the DAC 48, amplifies the received analog signal f1(t), and outputs the analog signal f2(t). The analog signal f2(t) is supplied to the speaker 50. Accordingly, a circuitry part constituted by the DAC 48 and power amplifier 49 operates as a circuitry part that generates the analog signal f2(t) to be supplied to the speaker 50 based on the digital signal M'(n).

The speaker 50 receives the analog signal f2(t) from the power amplifier 49, and outputs a sound corresponding to the received analog signal f2(t).

Accordingly, when the patient 80 utters the voice v3, the operator 81 can hear the voice v3 of the patient 80 through the speaker 50.

The digital signal M'(n) is also supplied to the subtracting section 63. The subtracting section 63 subtracts the digital signal M'(n) from the digital signal M(n) that the ADC 47 has output, and outputs the digital signal P(n). The digital signal P(n) is expressed by the following equation:

$$P(n) = M(n) - M'(n) \tag{11}$$

wherein since M'(n)≈M(n) (see EQ. (10)), EQ. (11) may be changed into the following equation:

$$P(n) = M(n) - M'(n)$$
$$\approx 0$$

Accordingly, in the second communication mode, the digital signal P(n) is P(n)≈0. Thus, the light-emission control section 32 decides that the operator 81 is uttering substantially no voice, and therefore, the light-emitting section 31 can be prevented from emitting light when the patient 80 utters the voice v3.

As described above, in the first communication mode (see FIG. 18), when the noise v4 occurs, it can be removed from the sound that the patient microphone 2 has received. Accordingly, the operator 81 can see the light-emitting section 31 while uttering a voice to thereby visually confirm a change of the number of energized light-emitting elements depending upon the loudness of the voice of the operator 81 in real-time, and therefore, can visually recognize at how much loudness the voice of the operator 81 is heard by the patient 80.

In the second communication mode (see FIG. 19), when the patient 80 utters the voice v3, the operator 81 can hear the voice of the patient 80. Moreover, the light-emitting section 31 emits no light when the patient 80 utters the voice v3, and therefore, it is possible to avoid light emission by the light-emitting section 31 in spite of the fact that the voice of the operator 81 is not output from the speaker 5.

In the present embodiment, the GT control section 21 and light-emission control section 32 are used to generate the control signal L(n) for controlling the light-emitting section 31 from the digital signal P(n). The GT control section 21 and light-emission control section 32, however, may be constructed as a single control section, which may be used to generate the control signal L(n) for controlling the light-emitting section 31 from the digital signal P(n).

The present embodiment describes a case in which the operator 81 is informed that his/her voice is being output from the speaker 5 by the light-emitting section 31. The method of informing the operator 81 that his/her voice is being output from the speaker 5 is not limited to the case above, and the operator 81 may be informed by a different method. Now as the other method, a case in which the display section 33 (see FIG. 1) on the gantry 100 is used will be described hereinbelow.

Figure 20:
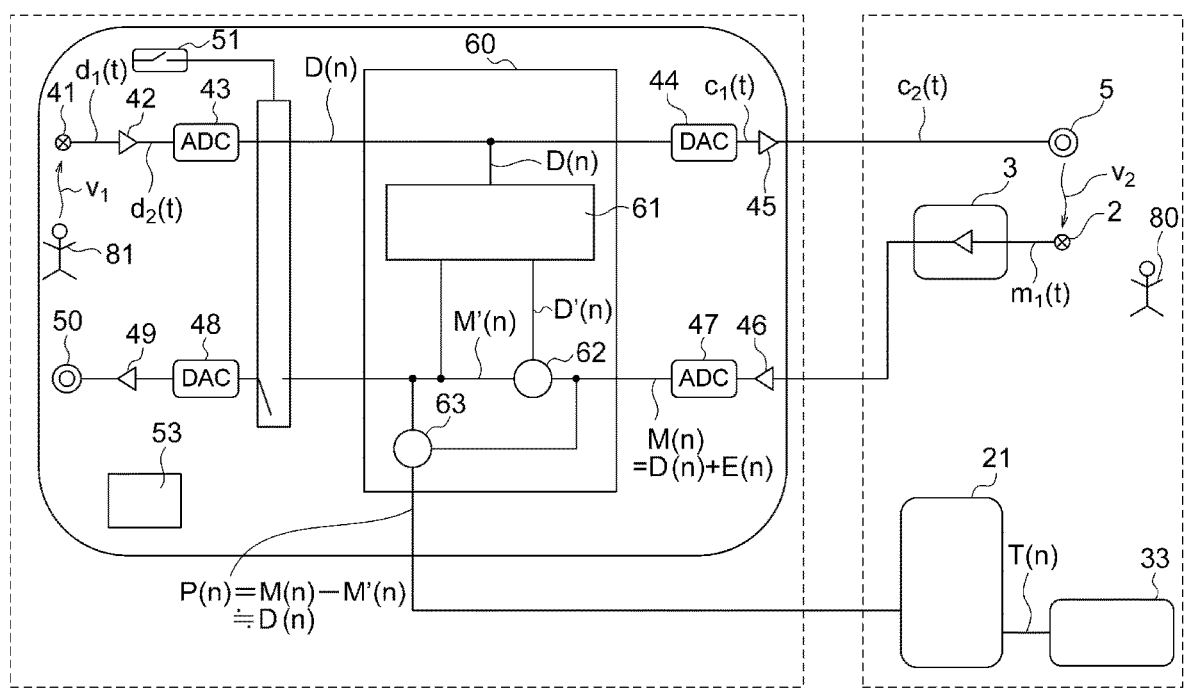
FIG. 20 is an explanatory diagram for a case in which the operator is informed that his/her voice is being output from the speaker by a display section on a gantry.

FIG. 20 is an explanatory diagram for the case in which the operator 81 is informed that his/her voice is being output from the speaker 5 by the display section 33 on the gantry 100.

The GT control section 21 receives the digital signal P(n), based on which it generates a control signal T(n) for controlling the display section 33. The display section 33 informs the operator 81 that his/her voice is being output from the speaker 5 based on the control signal T(n) (see FIG. 21).

Figure 21:
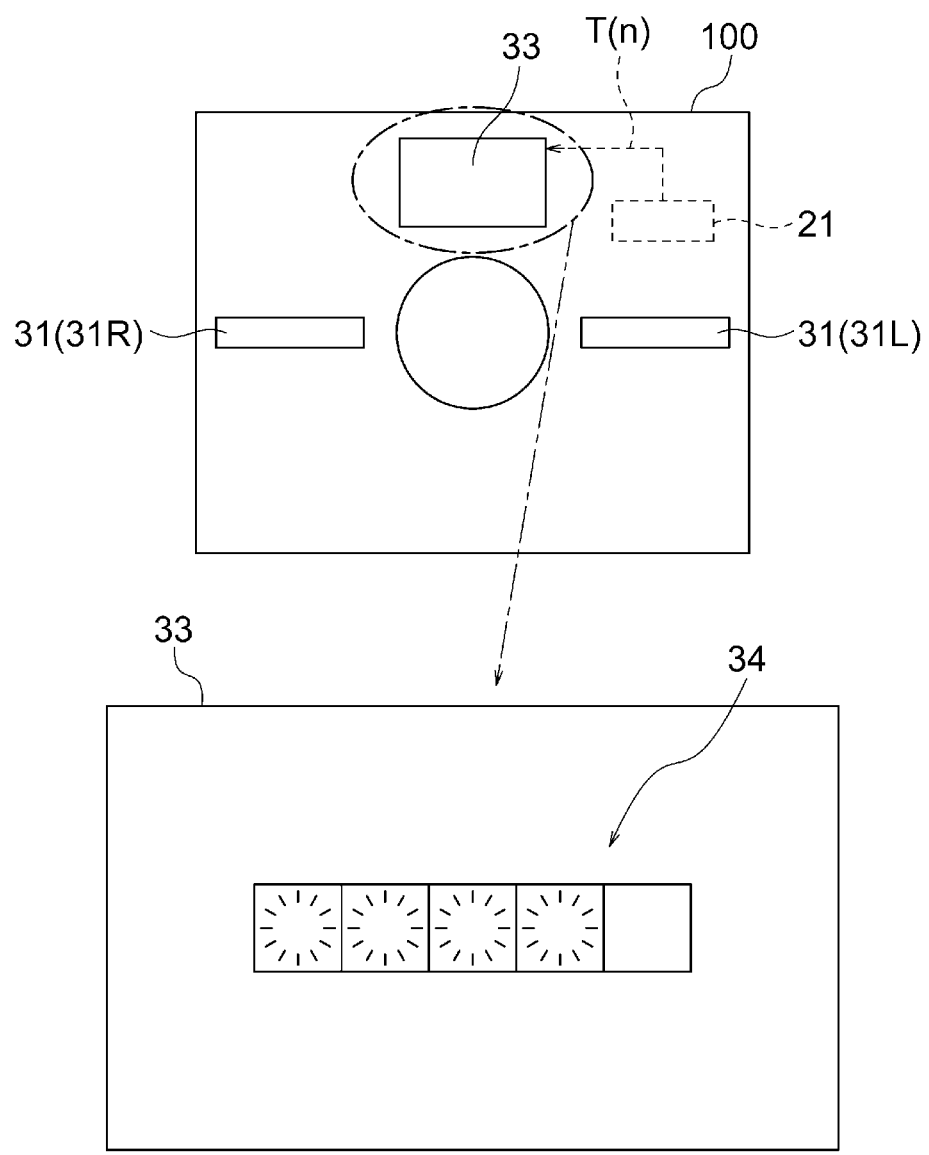
FIG. 21 is an enlarged view of the display section on the gantry.

FIG. 21 is an enlarged view of the display section 33 on the gantry 100.

On the display section 33 is displayed a level meter 34. The level meter 34 is divided into a plurality of areas. While the level meter 34 is shown to be divided into five areas in FIG. 21 for convenience of explanation, the level meter 34 may be divided into more than or less than five areas. Each area corresponds to a respective light-emitting element in the light-emitting section 31 (see FIG. 10). The level meter 34 indicates the loudness of the voice of the operator 81 by five levels: level 1 to level 5. In FIG. 21, a case in which the loudness of the voice of the operator 81 is at level 4 is shown.

In response to the control signal T(n), the display section 33 changes the level indicated by the level meter 34 so that the level corresponds to the loudness of the voice of the operator 81. Accordingly, the operator 81 can confirm whether or not his/her voice is being output from the speaker 5 by visually confirming the display section 33.

Figure 22:
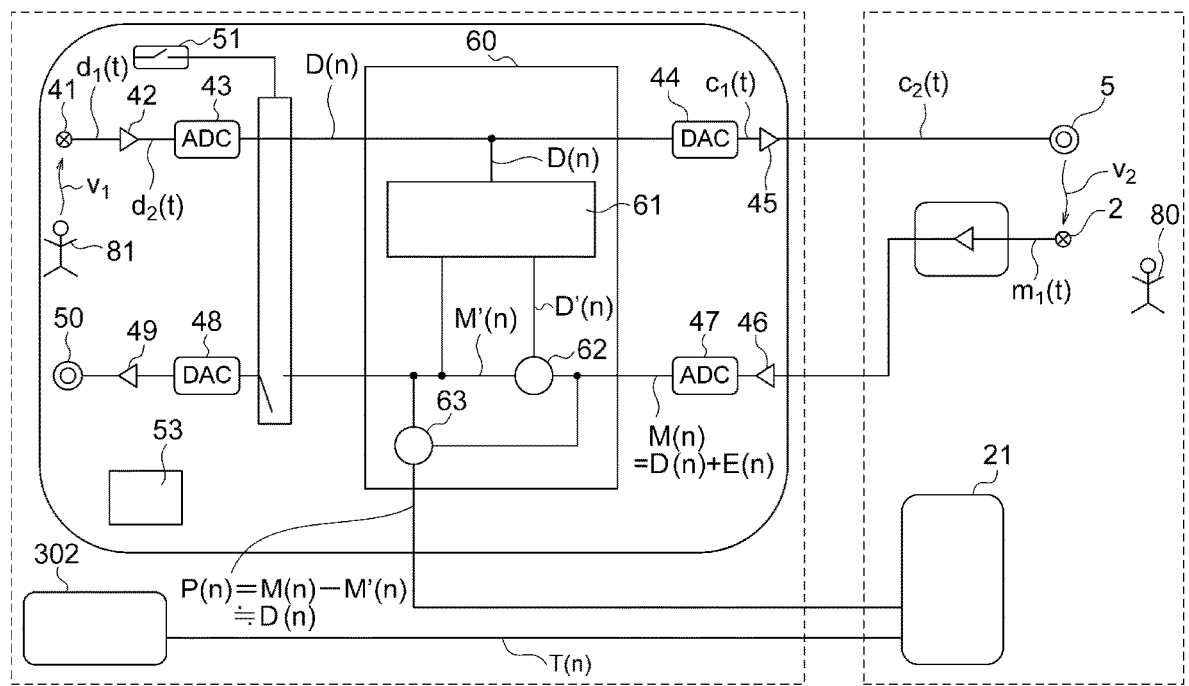
FIG. 22 is a diagram showing a case in which the operator is informed that the speaker has output the voice of the operator by a display device.

In FIG. 20 (and FIG. 21), the control signal T(n) is transmitted to the display section 33 on the gantry 100 to display the level meter 34 on the display section 33. The control signal T(n), however, may be transmitted to the display device 302 on the operator console 300 to display the level meter on the display device 302, as shown in FIG. 22.

Moreover, at least two or more of the light-emitting section 31, display section 33 on the gantry 100, and display device 302 on the operator console may be used to inform the operator 81 that his/her voice is being output from the speaker 5. Furthermore, the intercom module 4 may be provided with a display section to display information for informing the operator 81 whether or not his/her voice is being output from the speaker 5 on the display section on the intercom module 4.

While the present embodiment describes a case in which the light-emitting section 31 functioning as the level meter may be used to inform the operator 81 that his/her voice is being output from the speaker, a manner different from the level meter may be used insofar as it can inform the operator 81 that his/her voice is being output from the speaker.

Moreover, in the present embodiment, the number of energized light-emitting elements among the light-emitting elements e1 to e5 in the light-emitting section 31 is changed depending upon the loudness of the voice of the operator 81. The light-emitting section 31, however, may be constructed from only one light-emitting element, which is energized when the operator 81 utters a voice and not energized when the operator 81 is not uttering a voice.

Furthermore, in the present embodiment, communication between the operator 81 and patient 80 are implemented using the intercom module 4 capable of changing between the first communication mode and second communication mode with the microphone switch 51. The present invention is, however, not limited to the case in which the intercom module 4 described above is used, and it may be applied to a case in which a communication system capable of performing communication from the operator 81 to the patient 80 and that from the patient 80 to the operator 81 at the same time is used.

In the present embodiment, the filter block 60 is constructed from the adaptive filter 61, and subtracting sections 62 and 63. The filter block 60 is, however, not limited to this construction, and it may have a construction different from that of the adaptive filter 61, subtracting sections 62 and 63 insofar as noise may be removed from the sound received by the patient microphone 2. For example, the filter block 60 may be constructed using a computing section (e.g., an adding section, a multiplying section, or a dividing section) different from the subtracting section.

Moreover, in the present embodiment, a DSP is used as the filter block 60. In the present invention, however, the filter block 60 is not limited to the DSP and it may be implemented using circuitry, such as, for example, an FPGA (field-programmable gate array), different from the DSP.

Furthermore, in the present embodiment, the operator 81 visually confirms the light-emitting section 31 via the window 102 (see FIG. 1). The operator 81, however, may confirm the light emission state of the light-emitting section 31 by a method different from that of visually confirming the light-emitting section 31 via the window 102. For example, a camera for monitoring the inside of the scan room R1 may be provided to display the camera image on the display device in the operation room R2 so as to allow the operator 81 to visually confirm the light emission state of the light-emitting section 31.

In addition, while the scan room R1 and operation room R2 are separated from each other by the wall 101 in the present embodiment, the present invention is not limited to the case in which the scan room R1 and operation room R2 are separated from each other by the wall 101. For example, a corridor may be provided between the scan room R1 and operation room R2 so that the operator can walk there-through to move between the scan room R1 and operation room, instead of separating the scan room R1 operation room R2 by the wall 101. In this case, in order that the operator 81 can visually confirm the light emission state of the light-emitting section 31, windows for allowing the operator 81 to visually confirm the light emission state of the light-emitting section 31 may be provided in both the scan room R1 and operation room R2. Alternatively, a camera for monitoring the inside of the scan room R1 may be provided to display the camera image on the display device in the operation room R2 so as to allow the operator 81 to visually confirm the light emission state of the light-emitting section 31.

Moreover, in the present embodiment, the gantry 100 is provided with the light-emitting section 31 for visually informing the operator that his/her voice is being output from the speaker. The operator is, however, not necessarily visually informed insofar as the operator can recognize that his/her voice is being output from the speaker, and the operator may be informed by another way, for example, by an auditory way.

Furthermore, the present embodiment describes the case of the CT apparatus 1. The present invention, however, may be applied to any medical apparatus, such as an MRI apparatus or a SPECT apparatus, other than the CT apparatus 1, that requires communication between an operator and a patient.

What is claimed is:

1. A medical apparatus having:
   a first microphone installed in a first room for receiving a voice of an operator;
   a second microphone installed in a second room for receiving a voice of a patient;
   a first speaker installed in the first room for outputting the voice of the patient received by the second microphone;
   a second speaker installed in the second room for outputting the voice of the operator received by the first microphone; and
   a control section for controlling the informing of the operator, wherein a gantry is installed in the second room and comprises a light-emitting section for informing the operator.

2. The medical apparatus as recited in claim 1, wherein the operator is visually informed that the voice of the operator is being output from the second speaker.

3. The medical apparatus as recited in claim 2, wherein the second microphone has received the voice of the operator output from the second speaker, wherein the operator receives volume information representing a loudness of the voice of the operator.

4. The medical apparatus as recited in claim 1, wherein:
   the light-emitting section has a plurality of light-emitting elements, and
   the control section controls the plurality of light-emitting elements to change a number of the light-emitting elements that emit light and a number of the light-emitting elements that emit no light among the plurality of light-emitting elements depending upon the loudness of the voice of the operator.

5. The medical apparatus as recited in claim 4, wherein when the loudness of the voice of the operator is lower than a threshold, the plurality of light-emitting elements emit no light.

6. The medical apparatus as recited in claim 1, wherein:
   the gantry installed in the second room has a display section for informing the operator, and
   the control section controls the display section to display the volume information representing the loudness of the voice of the operator.

7. The medical apparatus as recited in claim 1, wherein:
   a display device for informing the operator is installed in the first room, and
   the control section controls the display device to display the volume information representing the loudness of the voice of the operator.

8. The medical apparatus as recited in claim 7, comprising:
   a filter block comprising:
   receiving a first digital signal containing sound data representing a sound that the first microphone has received;
   receiving a second digital signal containing sound data representing a sound that the second microphone has received;
   generating from the second digital signal a third digital signal representing signal components corresponding to noise; and
   generating a fourth digital signal containing sound data representing the voice of the operator by subtracting the third digital signal from the second digital signal, wherein the control section controls informing the operator based on the fourth digital signal.

9. The medical apparatus as recited in claim 8, wherein the filter block comprises:
   an adaptive filter for generating a fifth digital signal based on the first digital signal and the third digital signal;
   a first subtracting section for outputting the third digital signal by subtracting the fifth digital signal from the second digital signal; and
   a second subtracting section for generating the fourth digital signal by subtracting the third digital signal from the second digital signal.

10. The medical apparatus as recited in claim 9, wherein the adaptive filter adjusts its filter coefficients based on the third digital signal so that a difference between the first digital signal and the fifth digital signal comes close to zero.

11. The medical apparatus as recited in claim 10, further comprising an intercom module having the filter block.

12. The medical apparatus as recited in claim 11, wherein:
   the first microphone outputs a first analog signal representing a sound received by the first microphone, and
   the intercom module comprises:
   a first circuitry part for generating the first digital signal based on the first analog signal; and
   a second circuitry part for generating a second analog signal to be supplied to the second speaker based on the first digital signal.

13. The medical apparatus as recited in claim 12, wherein:
   the second microphone outputs a third analog signal representing a sound received by the second microphone, and
   the intercom module has a third circuitry part for generating the second digital signal based on the third analog signal.

14. The medical apparatus as recited in claim 13, wherein the intercom module is capable of implementing a first communication mode in which the first microphone is electrically connected to the second speaker, and moreover, the second microphone is electrically disconnected from the first speaker.

15. The medical apparatus as recited in claim 14, wherein the intercom module is capable of implementing a second communication mode in which the second microphone is electrically connected to the first speaker, and moreover, the first microphone is electrically disconnected from the second speaker.

16. The medical apparatus as recited in claim 15, wherein the intercom module has a microphone switch for changing the communication mode between the first communication mode and second communication mode.

17. The medical apparatus as recited in claim 16, wherein the intercom module is set to the second communication mode, and moreover, the patient utters a voice, the first speaker outputs the voice of the patient, and the control section decides that the operator utters no voice.

18. A program stored in a medical apparatus, the apparatus comprising: a first microphone installed in a first room for receiving a voice of an operator; a second microphone installed in a second room for receiving a voice of a patient; a first speaker installed in the first room for outputting the voice of the patient received by the second microphone; a second speaker installed in the second room for outputting the voice of the operator received by the first microphone; and informing, when the second microphone has received the voice of the operator output from the second speaker, informing the operator that the voice of the operator is being output from the second speaker, the program being for causing one or more processors to execute:

processing of receiving a first digital signal containing sound data representing a sound that the first microphone has received, and a second digital signal containing sound data representing a sound that the second microphone has received, generating from the second digital signal a third digital signal representing signal components corresponding to noise, and generating a fourth digital signal containing sound data representing the voice of the operator by subtracting the third digital signal from the second digital signal; and control processing of controlling the informing of the operator based on the fourth digital signal.

* * * * *